United States Patent
Freedman et al.

(10) Patent No.: US 12,296,197 B2
(45) Date of Patent: May 13, 2025

(54) MONITORING OF SYSTEM LATENCY ERRORS IN RADIOTHERAPY FOR CANCER TREATMENT

(71) Applicant: Elekta Limited, Crawley (GB)

(72) Inventors: Joshua Freedman, Crawley (GB); Fabienne Lathuiliere, Outremont (CA); Kevin John Brown, Crawley (GB); David Roberts, Crawley (GB); Sebastien Tremblay, Saint-Jean-sur-Richelieu (CA)

(73) Assignee: Elekta Limited, Crawley (GB)

( * ) Notice: Subject to any disclaimer, the term of this patent is extended or adjusted under 35 U.S.C. 154(b) by 0 days.

(21) Appl. No.: 18/309,114

(22) Filed: Apr. 28, 2023

(65) Prior Publication Data
US 2024/0115882 A1    Apr. 11, 2024

(30) Foreign Application Priority Data
Sep. 28, 2022    (GB) ..................... 2214208

(51) Int. Cl.
*A61N 5/10*    (2006.01)
*G06T 7/00*    (2017.01)
*G06T 7/38*    (2017.01)

(52) U.S. Cl.
CPC ......... *A61N 5/1049* (2013.01); *A61N 5/1065* (2013.01); *G06T 7/0012* (2013.01);
(Continued)

(58) Field of Classification Search
CPC ............... A61N 5/1049; A61N 5/1065; A61N 2005/1055; A61N 2005/1089
(Continued)

(56) References Cited

U.S. PATENT DOCUMENTS

| | | | | |
|---|---|---|---|---|
| 6,937,696 B1* | 8/2005 | Mostafavi | ............. | A61B 5/055 |
| | | | | 378/65 |
| 2003/0125622 A1* | 7/2003 | Schweikard | ........... | A61B 90/10 |
| | | | | 600/437 |

(Continued)

FOREIGN PATENT DOCUMENTS

JP    2006230673    9/2006

OTHER PUBLICATIONS

E. Yorke, G. Mageras, T. LoSasso, H. Mostafavi and C. Ling, "Respiratory gating of sliding window IMRT," Proceedings of the 22nd Annual International Conference of the IEEE Engineering in Medicine and Biology Society (Cat. No. 00CH37143), Chicago, IL, USA, 2000, pp. 2118-2121 vol. 3 (Year: 2000).*

(Continued)

*Primary Examiner* — Kathleen Y Dulaney
(74) *Attorney, Agent, or Firm* — Schwegman Lundberg & Woessner, P.A.

(57) ABSTRACT

Devices, systems and techniques are used for cancer treatment. An example control device may be configured to be communicatively coupled to a radiation source of a radiotherapy device and a position sensor of the radiotherapy device. The example control device may be used to calculate, for a sliding window of a radiotherapy treatment, a positional error between: a measured target position signal determined from a series of images and sampled at the acquisition times of the images, and an estimated target position signal. The example control device may generate a computer-executable instruction configured to alter the radiotherapy treatment in response to the positional error violating a threshold.

17 Claims, 15 Drawing Sheets

(52) U.S. Cl.
    CPC ........ *G06T 7/38* (2017.01); *A61N 2005/1055* (2013.01); *A61N 2005/1089* (2013.01)

(58) Field of Classification Search
    USPC ........................ 382/294, 128; 600/1; 378/65
    See application file for complete search history.

(56) References Cited

U.S. PATENT DOCUMENTS

| | | | |
|---|---|---|---|
| 2010/0046706 A1* | 2/2010 | Moreau | A61N 5/1047 378/65 |
| 2011/0200170 A1* | 8/2011 | Nord | A61N 5/1036 378/65 |
| 2011/0211665 A1* | 9/2011 | Maurer, Jr. | A61N 5/1039 378/19 |
| 2012/0253178 A1* | 10/2012 | Mostafavi | A61B 5/055 600/407 |
| 2012/0316423 A1 | 12/2012 | Raleigh et al. | |
| 2013/0123565 A1* | 5/2013 | Denis | A61N 5/1075 600/1 |
| 2015/0045604 A1* | 2/2015 | Sawkey | A61N 5/1068 600/1 |
| 2016/0023019 A1* | 1/2016 | Filiberti | A61N 5/1075 600/1 |
| 2018/0200535 A1 | 7/2018 | Froehlich et al. | |
| 2019/0069856 A1* | 3/2019 | Achkire | A61B 6/022 |
| 2019/0299029 A1* | 10/2019 | Inoue | A61N 5/1081 |
| 2020/0008707 A1* | 1/2020 | Li | A61B 5/055 |
| 2020/0043624 A1* | 2/2020 | Schnarr | A61N 5/1083 |
| 2020/0289853 A1* | 9/2020 | Friedman | A61N 5/1064 |
| 2021/0052186 A1* | 2/2021 | Mickevicius | A61B 5/055 |
| 2021/0205635 A1* | 7/2021 | Bokrantz | A61N 5/1031 |
| 2021/0267487 A1* | 9/2021 | Huang | A61B 5/7267 |
| 2022/0047893 A1* | 2/2022 | Wen | A61N 5/1031 |
| 2023/0051255 A1* | 2/2023 | Yan | A61N 5/1049 |
| 2023/0132237 A1* | 4/2023 | Xiang | A61N 5/1047 600/1 |

OTHER PUBLICATIONS

"European Application No. 203199471.6, Extended Search Report dated Feb. 16, 2024", (Feb. 16, 2024), 7 pgs.

* cited by examiner

MONITORING OF SYSTEM LATENCY ERRORS IN RADIOTHERAPY FOR CANCER TREATMENT

This disclosure relates to controlling radiotherapy devices, and in particular to controlling radiotherapy devices based on an error between measured and estimated positions of a target for cancer treatment.

BACKGROUND

Radiotherapy can be described as the use of ionising radiation, such as X-rays, to treat a human or animal body. Radiotherapy is commonly used to treat tumours within the body of a patient or subject. In such treatments, ionising radiation is used to irradiate, and thus destroy or damage, cells which form part of the tumour.

A radiotherapy device typically comprises a gantry which supports a beam generation system, or other source of radiation, which is rotatable around a patient. For example, for a linear accelerator (linac) device, the beam generation system may comprise a source of radio frequency energy, a source of electrons, an accelerating waveguide, beam shaping apparatus, etc.

In radiotherapy treatment, it is desirable to deliver a prescribed dose of radiation to a target region of a subject and to limit irradiation of other parts of the subject, i.e. to healthy tissue. Motion of the subject can cause a decreased dose to be applied to the target region and/or an increased dose to be applied to the healthy tissue. To address this, known techniques include monitoring a location of the subject and gating the treatment beam such that radiation is applied only when the subject (i.e. the target region within the subject) is in a desired location and not when the subject/target region is in a suboptimal location. This improves clinical outcomes.

There are various physiological motions that can contribute to a total motion of a subject. Discrete, gross or large-scale movements of a subject may include shifting position, coughing or sneezing. The subject may also undergo cyclical, physiological movement. For example, the subject may undergo respiratory motion due to their breathing cycle. The subject may also undergo cardiac motion based on beating of their heart. These motions can alter the location of a subject and/or of a tumour in a time-dependent manner relative to the respective location of the subject and/or of the tumour at the start of the radiotherapy treatment.

In a gated radiotherapy treatment, radiotherapy may only be delivered during a pre-defined window of a respiratory cycle based on a monitored position of a target. However, there is a system latency, i.e. a time delay, between anatomical positions of the subject and system responses to those positions. In other words, the monitoring indicates the anatomical positions of the subject at some time in the past. The delay may be several tenths of a second, for example between 300 ms and 400 ms. When using MR imaging for motion monitoring, increasing the speed of the MR imaging encounters the issue that there is a limit to how fast the imaging can be performed while meeting image quality requirements. One approach to dealing with such system latency is to use a prediction model, for example based on linear regression filters. The prediction model can be trained on the target waveform calculated from previously acquired data and then applied to infer the waveform at a future time, thereby effectively reducing the system latency by looking ahead to how the anatomy of the subject is expected to move at subsequent timepoints.

However, prediction modelling techniques can result in inference errors, particularly when applied to irregular motion, e.g. due to irregular respiratory patterns. This is because the motion deviates from the waveform previously followed. For example, a regular respiratory pattern may be associated with an approximately sinusoidal waveform. A prediction model may extrapolate from previous timepoints that the target will continue to follow this sinusoid at subsequent timepoints. However, if the subject moves suddenly or irregularly, for example due to coughing, sneezing, shifting position or hyperventilating, they will deviate from this sinusoid such that the prediction model will not have accurately projected the position of the target at the associated timepoints. Driving gating decisions based on such predicted positions with inference errors can thereby lead to incorrect gating decisions. This in turn can cause dosimetric errors whereby a decreased dose is applied to the target and/or an increased dose is applied to healthy tissue.

Continuing with a treatment when the risk of applying an increased dose to healthy tissue is high may be unsafe. Conversely, interrupting a treatment when the risk of applying an increased dose to healthy tissue is low may lead to inefficient treatment, long treatment times, discomfort of the subject and under-utilisation of the radiotherapy device. There is a need for improved responses to varying levels of risk associated with subject motion and control of a radiotherapy device.

It would be advantageous to provide improved means for accounting for changeable subject locations and system latency during a radiotherapy treatment. In addition, it would be advantageous to provide reliable and robust determination of when inference errors are merely small or inconsequential or transient errors, indicating that a radiotherapy treatment can continue, and when they are consequential, indicating that a radiotherapy treatment should be interrupted or altered. Therefore, there is a need for more reliable, more accurate, more efficient and/or safer control of a radiotherapy device.

The present invention seeks to address these and other disadvantages encountered in the prior art.

SUMMARY

An invention for cancer treatment is set out in the independent claims. Advantageous embodiments are set out in the dependent claims.

According to an aspect, there is provided a computer-implemented method comprising: calculating, for a sliding window of a radiotherapy treatment, a positional error between: a measured target position signal determined from a series of images and sampled at the acquisition times of the images; and an estimated target position signal; and generating a computer-executable instruction configured to alter the radiotherapy treatment in response to the positional error violating a threshold.

According to a further aspect, there is provided a computer-readable medium comprising computer-executable instructions which, when executed by a processor, cause the processor to perform the above-described methods.

According to a further aspect, there is provided a control device configured to be communicatively coupled to a radiation source of a radiotherapy device and a position sensor of the radiotherapy device, the control device comprising a processor and computer-executable instructions which, when executed by the processor, cause the control device to: calculate, for a sliding window of a radiotherapy treatment, a positional error between: a measured target position determined from a series of images and sampled at the acquisition times of the images and an estimated target position signal; and generate a computer-executable instruction configured to alter the radiotherapy treatment in response to the positional error violating a threshold.

According to a further aspect, there is provided a radiotherapy device comprising: the above-described control device; a radiation source configured to generate a radiotherapy beam for the radiotherapy treatment; and a position sensor configured to determine the measured target position signal.

BRIEF DESCRIPTION OF THE DRAWINGS

Specific embodiments are now described, by way of example only, with reference to the drawings, in which.

DETAILED DESCRIPTION

A prediction model can be trained to predict the future motion of a patient, for example due to respiration. The predictions can be used to reduce system latency, but may result in inference errors when applied to irregular respiratory patterns. This in turn may lead to incorrect gating decisions and dosimetric errors. There is a need for reliably determining whether the inference errors are consequential or merely small, inconsequential or transient. A risk control measure has been developed to monitor the accuracy of a prediction model. Measured and estimated target positions are considered over a sliding time window. The measured target position is determined from a series of images and sampled at the acquisition times of the images (to negate the latency associated with transmission and processing of the images). In other words, the measured target position signal sampled at the acquisition times of the images provides the position of the target at a series of timepoints at which images were acquired, rather than at some later timepoints with a delay due to system latency. The timepoints of the estimated target position signal may correspond to the timepoints of the measured target position signal sampled at the acquisition times of the images to enable comparison of these signals. A positional error between the measured target positions (sampled at the image acquisition times) and estimated target positions is calculated, for example based on comparing the absolute means and standard deviations of the measured and estimated target positions. This positional error is compared to a threshold to determine whether to alter or interrupt the radiotherapy treatment. An error violating the threshold may indicate that the patient has deviated significantly from the anticipated motion, for example due to coughing or other sudden, irregular motion. An error not violating the threshold may indicate that the patient has not deviated significantly from the anticipated motion such that treatment can continue. This provides more accurate, efficient and reliable control of the radiotherapy device in consideration of potential movement of the subject.

Figure 1:
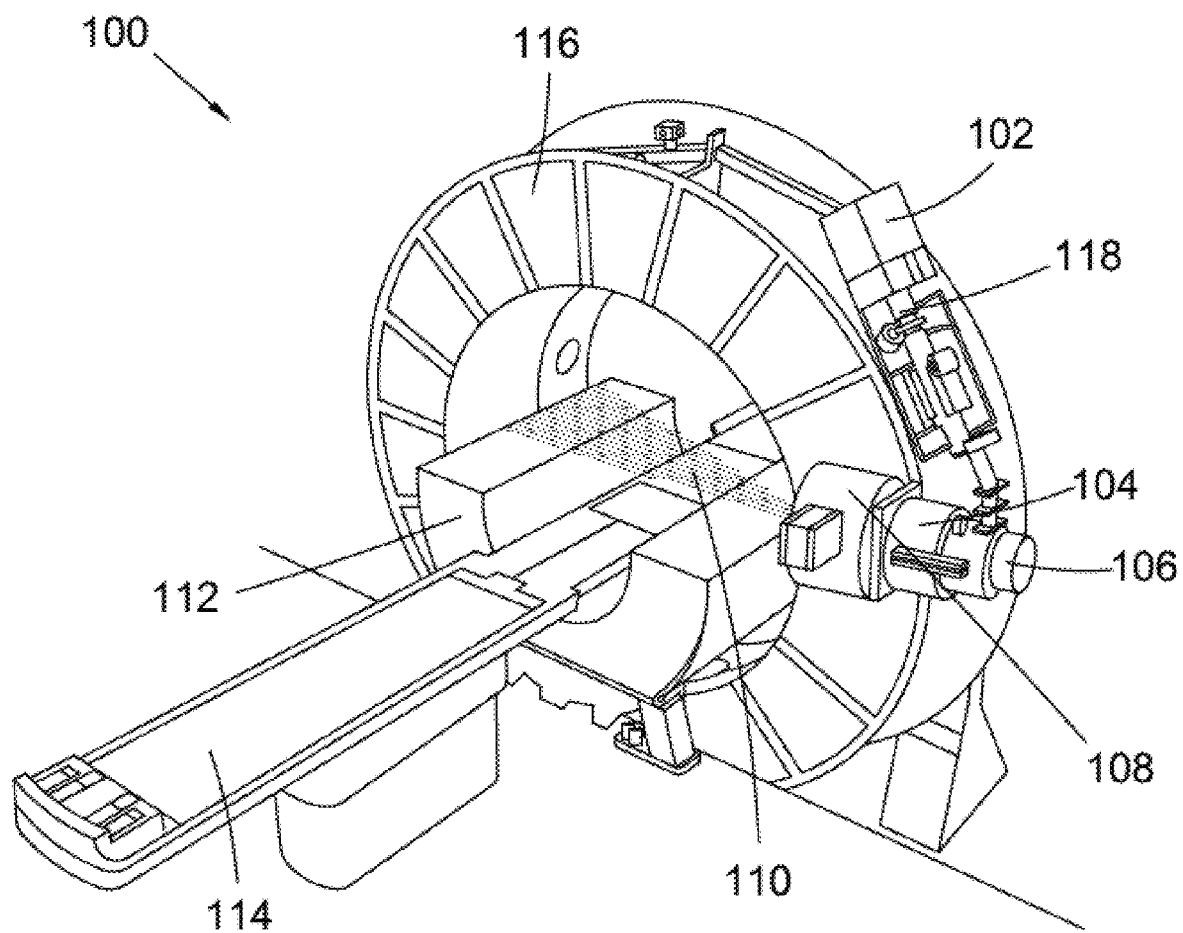
FIG. 1 depicts a radiotherapy device or apparatus according to the present disclosure.

FIG. 1 depicts a radiotherapy device suitable for delivering, and configured to deliver, a beam of radiation to a patient during radiotherapy treatment. The device and its constituent components will be described generally for the purpose of providing useful accompanying information for the present invention. The device depicted in FIG. 1 is in accordance with the present disclosure and is suitable for use with the disclosed systems and apparatuses. While the device in FIG. 1 is an MR-linac, the implementations of the present disclosure may be any radiotherapy device, for example a linac device.

The device 100 depicted in FIG. 1 is an MR-linac. The device 100 comprises both MR imaging apparatus 112 and radiotherapy (RT) apparatus which may comprise a linac device. The MR imaging apparatus 112 is shown in cross-section in the diagram. In operation, the MR scanner produces MR images of the patient, and the linac device produces and shapes a beam of radiation and directs it toward a target region within a patient's body in accordance with a radiotherapy treatment plan. The depicted device does not have the usual 'housing' which would cover the MR imaging apparatus 112 and RT apparatus in a commercial setting such as a hospital.

The MR-linac device depicted in FIG. 1 comprises a source of radiofrequency waves 102, a waveguide 104, a source of electrons 106, a source of radiation 106, a collimator 108 such as a multi-leaf collimator configured to collimate and shape the beam, MR imaging apparatus 112, and a patient support surface 114. In use, the device would also comprise a housing (not shown) which, together with the ring-shaped gantry, defines a bore. The moveable support surface 114 can be used to move a patient, or other subject, into the bore when an MR scan and/or when radiotherapy is to commence. The MR imaging apparatus 112, RT apparatus, and a subject support surface actuator are communicatively coupled to a controller or processor. The controller is also communicatively coupled to a memory device comprising computer-executable instructions which may be executed by the controller. As used herein, a controller may also be referred to as a control device.

The RT apparatus comprises a source of radiation and a radiation detector (not shown). Typically, the radiation detector is positioned diametrically opposed to the radiation source. The radiation detector is suitable for, and configured to, produce radiation intensity data. In particular, the radiation detector is positioned and configured to detect the intensity of radiation which has passed through the subject. The radiation detector may also be described as radiation detecting means, and may form part of a portal imaging system.

The radiation source may comprise a beam generation system. For a linac, the beam generation system may comprise a source of RF energy 102, an electron gun 106, and a waveguide 104. The radiation source is attached to the rotatable gantry 116 so as to rotate with the gantry 116. In this way, the radiation source is rotatable around the patient so that the treatment beam 110 can be applied from different angles around the gantry 116. In a preferred implementation, the gantry is continuously rotatable. In other words, the gantry can be rotated by 360 degrees around the patient, and in fact can continue to be rotated past 360 degrees. The gantry may be ring-shaped. In other words, the gantry may be a ring-gantry.

The source 102 of radiofrequency waves, such as a magnetron, is configured to produce radiofrequency waves. The source 102 of radiofrequency waves is coupled to the waveguide 104 via circulator 118, and is configured to pulse radiofrequency waves into the waveguide 104. Radiofrequency waves may pass from the source 102 of radiofrequency waves through an RF input window and into an RF input connecting pipe or tube. A source of electrons 106, such as an electron gun, is also coupled to the waveguide 104 and is configured to inject electrons into the waveguide 104. In the electron gun 106, electrons are thermionically emitted from a cathode filament as the filament is heated. The temperature of the filament controls the number of electrons injected. The injection of electrons into the waveguide 104 is synchronised with the pumping of the radiofrequency waves into the waveguide 104. The design and operation of the radiofrequency wave source 102, electron source and the waveguide 104 is such that the radiofrequency waves accelerate the electrons to very high energies as the electrons propagate through the waveguide 104.

The design of the waveguide 104 depends on whether the linac accelerates the electrons using a standing wave or travelling wave, though the waveguide typically comprises a series of cells or cavities, each cavity connected by a hole or 'iris' through which the electron beam may pass. The cavities are coupled in order that a suitable electric field pattern is produced which accelerates electrons propagating through the waveguide 104. As the electrons are accelerated in the waveguide 104, the electron beam path is controlled by a suitable arrangement of steering magnets, or steering coils, which surround the waveguide 104. The arrangement of steering magnets may comprise, for example, two sets of quadrupole magnets.

Once the electrons have been accelerated, they may pass into a flight tube. The flight tube may be connected to the waveguide by a connecting tube. This connecting tube or connecting structure may be called a drift tube. The electrons travel toward a heavy metal target which may comprise, for example, tungsten. Whilst the electrons travel through the flight tube, an arrangement of focusing magnets act to direct and focus the beam on the target.

To ensure that propagation of the electrons is not impeded as the electron beam travels toward the target, the waveguide 104 is evacuated using a vacuum system comprising a vacuum pump or an arrangement of vacuum pumps. The pump system is capable of producing ultra-high vacuum (UHV) conditions in the waveguide 104 and in the flight tube. The vacuum system also ensures UHV conditions in the electron gun. Electrons can be accelerated to speeds approaching the speed of light in the evacuated waveguide 104.

The source of radiation is configured to direct a beam 110 of therapeutic radiation toward a patient positioned on the patient support surface 114. The source of radiation may comprise a heavy metal target toward which the high energy electrons exiting the waveguide are directed. When the electrons strike the target, X-rays are produced in a variety of directions. A primary collimator may block X-rays travelling in certain directions and pass only forward travelling X-rays to produce a treatment beam 110. The X-rays may be filtered and may pass through one or more ion chambers for dose measuring. The beam can be shaped in various ways by beam-shaping apparatus, for example by using a multi-leaf collimator 108, before it passes into the patient as part of radiotherapy treatment.

In some implementations, the source of radiation is configured to emit either an X-ray beam or an electron particle beam. Such implementations allow the device to provide electron beam therapy, i.e. a type of external beam therapy where electrons, rather than X-rays, are directed toward the target region. It is possible to 'swap' between a first mode in which X-rays are emitted and a second mode in which electrons are emitted by adjusting the components of the linac. In essence, it is possible to swap between the first and second mode by moving the heavy metal target in or out of the electron beam path and replacing it with a so-called 'electron window'. The electron window is substantially transparent to electrons and allows electrons to exit the flight tube.

The subject or patient support surface 114 is configured to move between a first position substantially outside the bore, and a second position substantially inside the bore. In the first position, a patient or subject can mount the patient support surface. The support surface 114, and patient, can then be moved inside the bore, to the second position, in order for the patient to be imaged by the MR imaging apparatus 112 and/or imaged or treated using the RT apparatus. The movement of the patient support surface is effected and controlled by a subject support surface actuator, which may be described as an actuation mechanism. The actuation mechanism is configured to move the subject support surface in a direction parallel to, and defined by, the central axis of the bore. The terms subject and patient are used interchangeably herein such that the subject support surface can also be described as a patient support surface. The subject support surface may also be referred to as a moveable or adjustable couch or table.

The radiotherapy apparatus/device depicted in FIG. 1 also comprises MR imaging apparatus 112. The MR imaging apparatus 112 is configured to obtain images of a subject positioned, i.e. located, on the patient support surface 114. The MR imaging apparatus 112 may also be referred to as the MR imager. The MR imaging apparatus 112 may be a conventional MR imaging apparatus operating in a known manner to obtain MR data, for example MR images. The skilled person will appreciate that such a MR imaging apparatus 112 may comprise a primary magnet, one or more gradient coils, one or more receive coils, and an RF pulse applicator. The operation of the MR imaging apparatus is controlled by the controller. While the discussion herein may focus on MR imaging by way of example, alternatively or in addition to MR imaging, one or more other imaging techniques, modalities, sensors or detectors may be used, such as CT/X-ray, PET, optical imaging/cameras, infra-red imaging, ultra-sound imaging or time-of-flight techniques. Any one or more of these may be used to determine the position of the target. As used herein, references to determining the position of the target may be used interchangeably with determining the position of the subject or of a part of the subject.

The controller is a computer, processor, or other processing apparatus. The controller may be formed by several discrete processors; for example, the controller may comprise a processor for each of the various individual components of the radiotherapy device as described herein. The controller is communicatively coupled to a memory, e.g. a computer readable medium. The controller may be communicatively coupled to one, multiple or all of the various individual components of the radiotherapy device as described herein. As used herein, the controller may also be referred to as a control device.

The linac device also comprises several other components and systems as will be understood by the skilled person. For example, in order to ensure the linac does not leak radiation, appropriate shielding is also provided.

The radiotherapy device and/or the control device may be configured to perform any of the method steps presently disclosed and may comprise computer executable instructions which, when executed by a processor cause the processor to perform any of the method steps presently disclosed, or when executed by the control device cause the control device to perform any of the method steps presently disclosed, or when executed by the radiotherapy device cause the radiotherapy device to perform any of the method steps presently disclosed. Any of the steps that the radiotherapy device and/or the control device is configured to perform may be considered as method steps of the present disclosure and may be embodied in computer executable instructions for execution by a processor. A computer-readable medium may comprise the above-described computer executable instructions.

A position of a target within a subject may be measured, monitored or determined during a radiotherapy treatment. This may be performed using a position sensor, for example an imaging apparatus such as an MR imaging apparatus. As the skilled person will be familiar with, MR imaging is an imaging technique which involves placing a subject in a strong magnetic field which aligns the magnetic moments of protons in the subject to produce a net magnetization. Irradiating the subject with radiofrequency (RF) pulses of a particular resonant frequency tips the net magnetization of these protons by a flip-angle $\alpha°$ into a plane perpendicular to the strong magnetic field. Immediately after the RF pulse is completed, the tipped net magnetization of these protons realigns with the strong magnetic field. The changing magnetic flux generated during realignment induces a voltage in a coil. This is measured and analysed to provide information on the distribution of different tissues within the subject.

However, there is a time delay or latency between a target being in a particular location and action being taken based on sensing of the target being in that location. For example, for MR imaging, this latency may include contributions from the duration or frequency of acquisition, the duration of reconstruction of an image, the preparation of the image for transmission, the transmission of the image to a motion manager, the determination of a decision based on the image and reference data/pre-determined conditions, and the response time of the radiotherapy device to alter or interrupt the treatment. These contributions entail that the response to the target being in a particular location is based on the location of the target at some point in the past, i.e. in the past by a time period referred to as the system latency. If the target moves during this time period, the use of such out of date information may lead to incorrect or inaccurate responses, which can cause dosimetric errors.

One technique for managing the system latency is to use a prediction model to anticipate where the target is likely to be at subsequent timepoints based on previous timepoints. Thus, a prediction model can predict where the target is likely to be at the current time based on measurements that reflect where the target was at a previous time or times. A system latency may be experimentally measured and/or calculated from operational data and/or log outputs from one or more components of the system. An output of a detector may be re-sampled at the time when the centre of k-space for each output signal value was actually acquired, such that the latency compensated detector output correctly describes the target positions at the correct times. However, while this compensated detector output is spatially and temporally accurate, it may only be retrospectively calculated for timepoints in the past by at least the system latency, rather than providing true real-time information.

A prediction signal may be determined based on the detector output. The prediction signal predicts, infers, extrapolates or projects the estimated or forecasted target position at subsequent timepoints based on the detector output at previous timepoints. In some examples, the prediction signal may be based on all previous timepoints for a radiotherapy treatment, or may be based on all previous timepoints for multiple radiotherapy treatments involving the same patient or multiple patients. In some examples, the prediction signal may be based on all previous timepoints corresponding to one or more respiratory cycles of the subject. In some examples, the prediction signal may be based on an integer number of previous timepoints. In some examples, the prediction model may make use of curve fitting and/or machine learning (including deep learning) techniques to determine the prediction signal.

An anatomical position monitoring (APM) algorithm may be used to indicate the target position based on the detector output. As used herein, the term APM signal refers to the measured target position signal. The term $APM_{k0}$ refers to the measured target position signal sampled at the acquisition times of the images, i.e. re-sampled at the times where the k-space centre points were acquired. The $APM_{k0}$ term may be referred to as being associated with an 'ideal' machine, i.e. being ideal in that it describes a scenario in which the measured target positions are known in real-time without system latency. As used herein, the term predicted signal, $Pred_{k0}$ refers to the estimated target position signal. The label $Pred_{k0}$ is used in acknowledgement that the predicted signal is determined based on the APM signal and that it is sampled at the acquisition times of the images, i.e. the times where k-space centre points are acquired.

This term may be referred to as being associated with an 'actual' machine, i.e. being actual in that it describes the real operating scenario in which target positions must be predicted in order to compensate for the system latency. In some examples, the term estimated target position signal may be used to refer to the APM (output) signal APM, i.e. to the APM signal without being shifted in time. In such examples, this APM signal may be 'estimated' in that it provides simplistic or first-order indication of where the target position is expected to be (without accounting for the non-zero system latency). The measured target position signal and the estimated target position signal may vary with respect to time during a radiotherapy treatment due to movement of the subject or a part of the subject, for example due to respiration of the subject. The estimated target position signal may be described as an expected target position signal, a predicted target position signal, an effective target position signal, an extrapolated target position signal, a gating decision target position signal or a target position signal used by the gating algorithm.

Figure 2A:
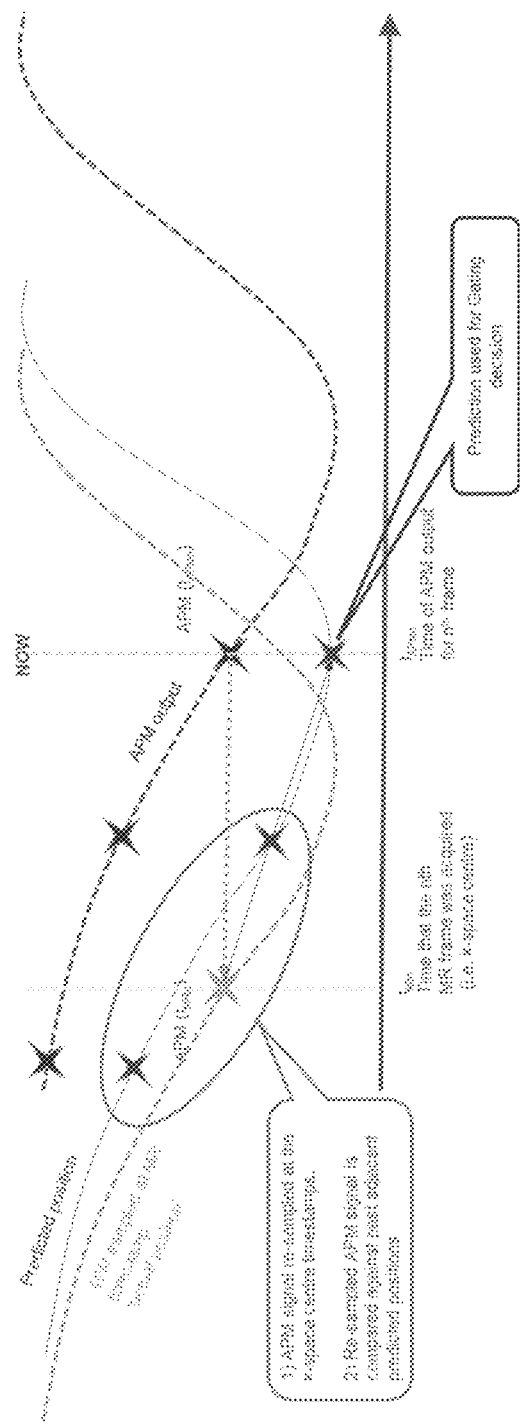
FIG. 2A depicts position signals for a system with latency according to the present disclosure.

FIG. 2A depicts an example of the above-mentioned considerations relating to system latency in graphical form. The APM output signal (dark dashed line in FIG. 2A) corresponds to the detector output. Due to the system latency, the APM output signal in fact describes anatomical positions in the past by a time period corresponding to the system latency. The $APM_{k0}$ signal (light dashed line in FIG. 2A) is the APM output signal re-sampled at the centre of k-space positions. The $APM_{k0}$ signal therefore corresponds to the shifted detector output and correctly describes the target positions at the correct times. The predicted signal (solid line in FIG. 2A) is inferred from the APM signal and predicts the target locations at future timepoints. At the time NOW, the prediction signal is available because it was inferred from previous measurements, whereas the $APM_{k0}$ signal is not yet available because it is only available for timepoints in the past by at least the system latency, and the APM output is available but describes out of date target positions. Therefore, at the time NOW, the prediction model attempts to provide a prediction signal which corresponds as closely as possible to the form the $APM_{k0}$ signal will take when data for this signal is available for the time NOW.

Figure 2B:
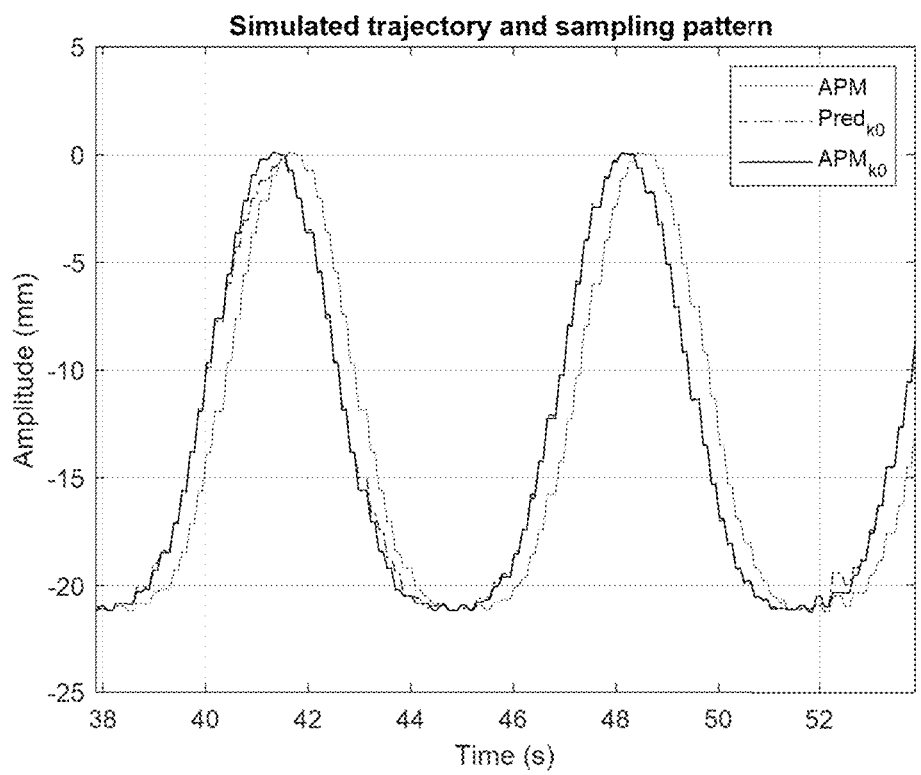
FIG. 2B depicts an example of a simulated trajectory of a target for a regular respiratory pattern according to the present disclosure.

FIG. 2B depicts an example of a simulated trajectory of a target for a regular respiratory pattern. The $APM_{k0}$ signal (dark solid time in FIG. 2B) has been calculated by resampling the APM (light solid line in FIG. 2B) at the centre of k-space positions. Since the example considered in FIG. 2B is a highly regular sinusoidal waveform, a prediction model is able to predict target locations at subsequent timepoints with a high level of accuracy. The predicted signal (light dot dash line in FIG. 2B) therefore closely approximates the $APM_{k0}$ signal, though slight deviations are visible particularly around turning points of the waveform, for example at approximately 41 s, 43.5 s and 52.5 s in FIG. 2B. These deviations shown in FIG. 2B may be acceptable in that a radiotherapy treatment may safely continue, i.e. they may be within a threshold or tolerance. However, for less regular waveforms, as will be discussed below, the predicted signal may deviate more significantly from the $APM_{k0}$ signal.

The techniques described herein may be implemented as part of the control of a radiotherapy device. The techniques described herein may be performed during a radiotherapy treatment/to control a radiotherapy treatment in real-time. The techniques described below may be implemented as simulations to test and/or verify radiotherapy treatments and/or the risk control measures described herein. Data may be incorporated from treatment of patients and/or from testing based on one or more phantoms, which may help test, calibrate and verify the described techniques.

Processing of waveforms associated with target motion will now be considered. The following three waveforms may be defined: the APM (APM), the APM re-sampled at k-space centre positions ($APM_{k0}$), the prediction at k-space centre positions ($Pred_{k0}$). The $APM_{k0}$ waveform may retrospectively be calculated by re-sampling the APM waveform according to variable system latency values $\Delta L$. This may comprise re-assigning the APM signal outputs at the centre of k-space timestamps:

$$T_{k0} = T_{APM} - \Delta L$$

$$APM_{k0}(T_{APM_{k0}}) = APM(T_{APM})$$

The $Pred_{k0}$ signal may be calculated by applying the prediction operator to the APM signal. Here, $T_{k0}$ represents the timestamps when the centre of k-space target positions were actually sampled. The $APM_{k0}$ and $Pred_{k0}$ signals may be sub-sampled (nearest neighbour), for example to a time-resolution of 80 ms, which may be close to the linac system clock resolution (which may by way of example be 40 ms).

Gating of a radiotherapy treatment will now be considered by way of example to illustrate the techniques described herein and the advantages thereof. However, it will be understood that the presently described techniques are also applicable to radiotherapy treatments which do not involve gating. For example, the presently described techniques are also applicable to radiotherapy treatments involving tracking of the radiotherapy beam.

A gating window may be calculated based on the APM signal:

$$G_{lower} = \text{Argmax}_t(APM) - G_{win} \quad G_{upper} = \text{Argmax}_t(APM)$$

The gating window size ($G_{win}$) may be set as an amplitude corresponding to a fraction of the total APM signal range, for example to 20% of the APM signal range. $G_{lower}$ indicates the lower boundary of the gating window and $G_{upper}$ indicates the upper boundary of the gating window. The $\text{Argmax}_t$ operations select the index of the APM signal at which the signal is at its maximum amplitude. Radiotherapy treatment may be delivered within the gating window, i.e. between $G_{lower}$ and $G_{upper}$, and may not be delivered, i.e. the beam may be held, outside the gating window. In this example, radiotherapy is only delivered in the top 20% of the APM signal range. However, it will be understood that this is used by way of non-limiting example and that many different treatment schemes may be used with differing gating and respiratory approaches. Gating based on the $APM_{k0}$ and $Pred_{k0}$ may each be considered. Here W, will be used in the following explanation to symbolize $APM_{k0}$ or $Pred_{k0}$.

Based on the amplitude values of W, dose may be delivered using a square field to the centre of a gating window at exhalation, i.e. to $$\frac{1}{2}(G_{lower} + G_{upper}).$$

The irradiated square field may have dimensions equivalent to the gross tumour volume (GTV)+$G_{win}$. However, it will be understood that this is used by way of non-limiting example and that many different treatment schemes may be used with differing gating and respiratory approaches. The GTV may vary for different targets/different subjects.

A dose rate may be described in units of monitor units (MU) per minute, i.e. $\text{MUmin}^{-1}$. As will be familiar to the skilled person, a monitor unit is a measure of machine output from a linear accelerator. Alternatively, the techniques described herein may be performed using other units of measurement, for example Gray or Rads. In an example, a dose rate may be chosen as 450 $\text{MUmin}^{-1}$ and a total delivery time may be chosen as 30 seconds. Radiotherapy may be applied when the amplitude of W is bounded by the gating window:

$$G_{lower} < W < G_{upper}$$

$$G_W = 1$$

Where $G_W$ is used to denote a binary gating signal. The delivery may remain ungated until the W signal amplitude is outside the gating window:

$W(t) < G_{lower}$ $G_W = 0$

Figure 3A:
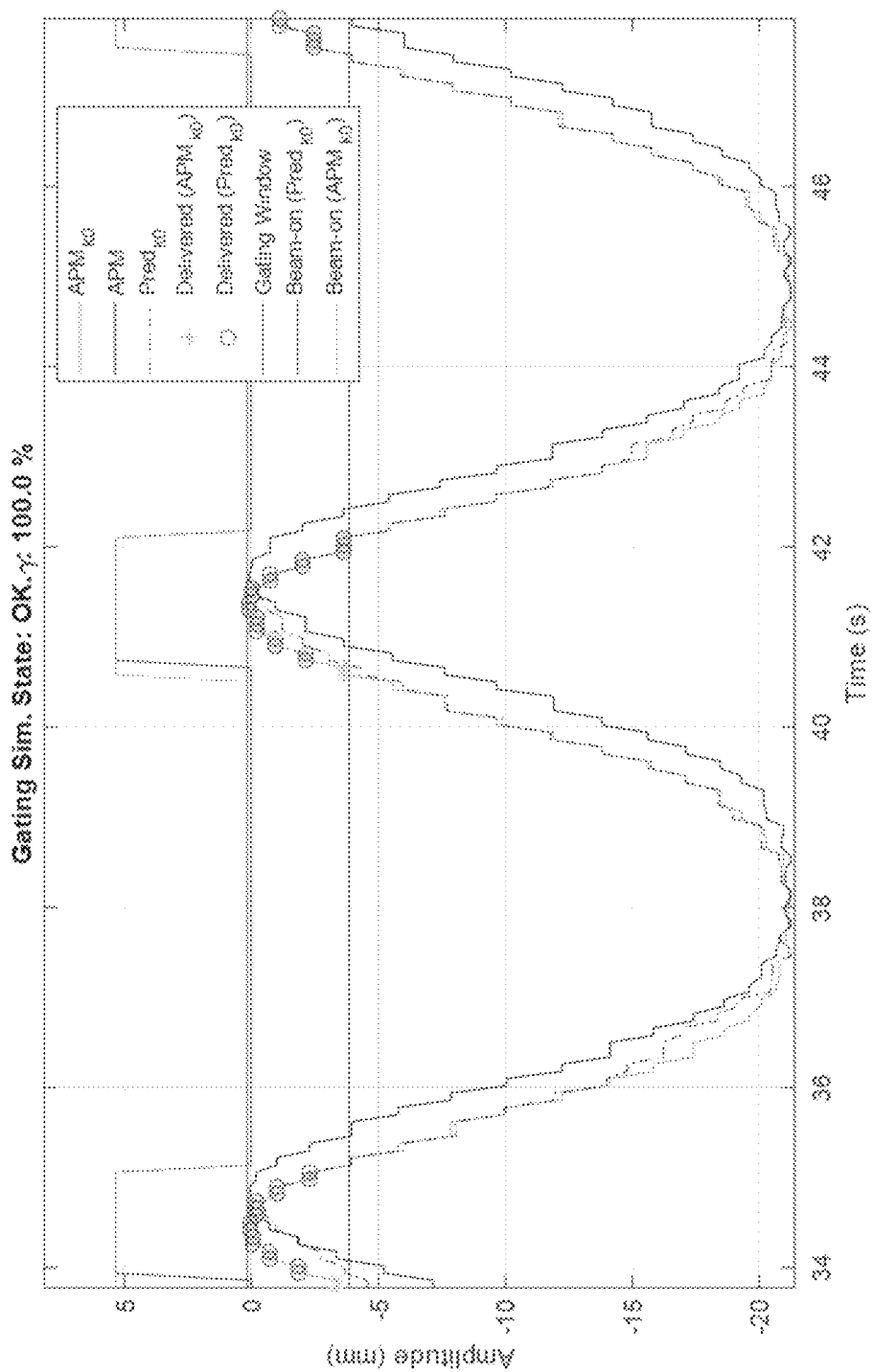
FIG. 3A depicts position and control signals for an example gated treatment according to the present disclosure.
Figure 3B:
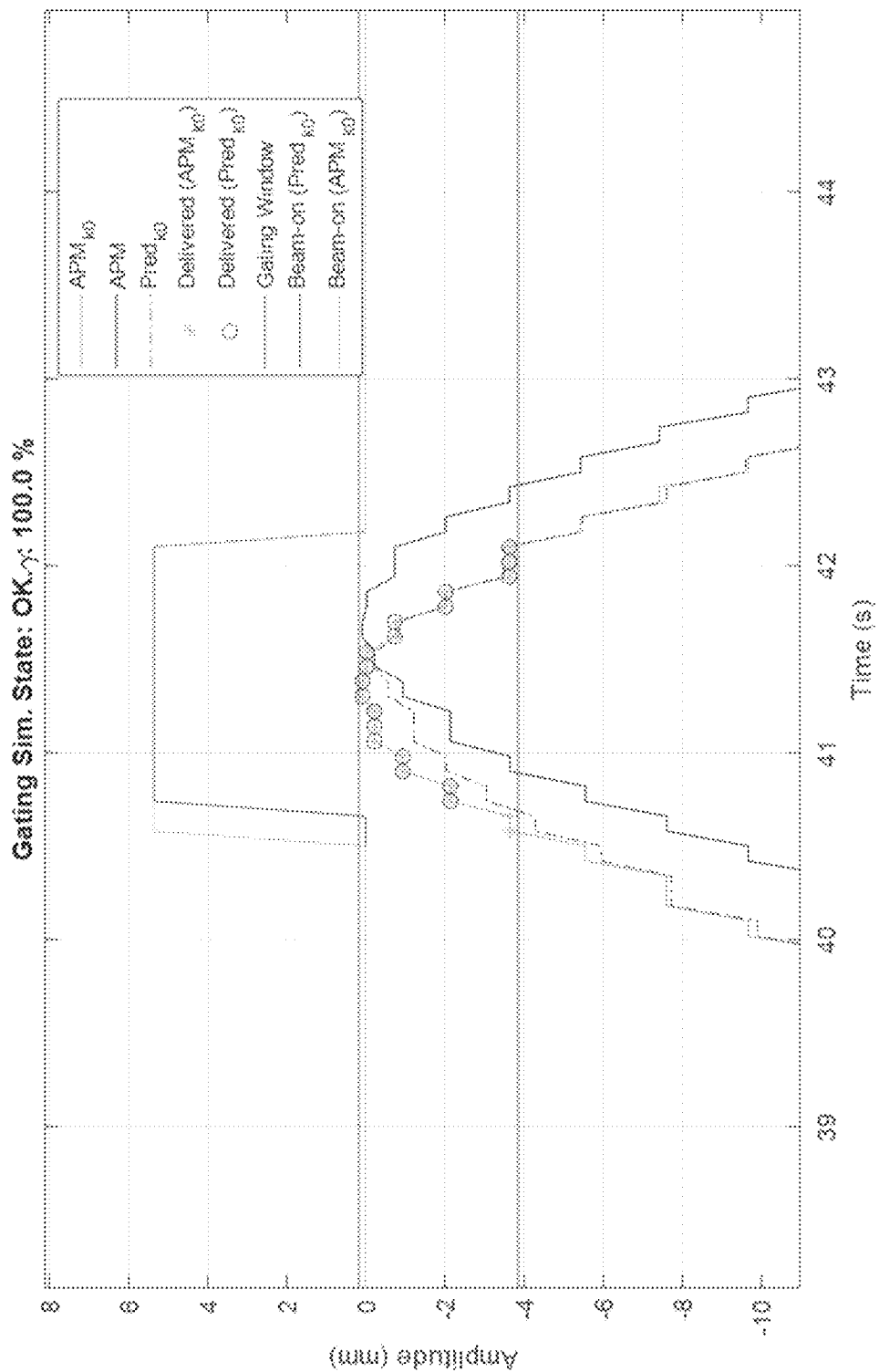
FIG. 3B depicts an expanded view of a subset of FIG. 3A according to the present disclosure.

FIGS. 3A and 3B shows an example gated treatment. FIG. 3B displays a magnified view of a subset of FIG. 3A. Here, the $APM_{k0}$ signal crosses the gating window before the $Pred_{k0}$ signal. This means that, over the period 40 to 43 seconds, gating based on $Pred_{k0}$ (estimated target position signal) under-delivers dose when compared to gating based on $APM_{k0}$ (measured target position signal). In other words, performing this gated treatment based on the output of the prediction model to compensate for system latency is found to under-deliver dose relative to a situation where the correct, real-time target locations are known and responded to immediately with no system latency. Note that the delivery device records the dose delivered and would have accounted for the under-delivery during the 40 to 43 second interval by delivering dose at a later time. However, this would have resulted in a longer treatment duration and consequently reduced treatment efficiency.

There is a need for reliable and robust determination of when such deviations between estimated and measured signals are inconsequential or transient, indicating that a radiotherapy treatment can continue, and when they are consequential, indicating that a radiotherapy treatment should be interrupted or altered.

Determination of the error between estimated and measured target positions signals will now be considered. Spatial errors may be dynamically calculated over a sliding dosimetric window $D_w$ of size:

$D_w = d_b - d_a$

Where $d_a$ and $d_b$ are MU values. Parameterising the window in terms of dose enables more direct relevance to the application of radiotherapy treatment by the radiotherapy device, which may in some examples vary the dose rate such that the dose applied is non-linear with time. The dosimetric window may operate on a first-in first-out approach, i.e. may consider the first points at which the dose is respectively equal to or greater than $d_a$ and greater than or equal to $d_b$. Based on the sliding dosimetric window, positions ($Pos_{ideal}$) may be calculated for the ideal machine, i.e. using the measured target position signals, and positions ($Pos_{actual}$) may be calculated for the actual machine, i.e. using the estimated target position signals.

For the ideal machine/the measured target position signals, the target was within the gating window, as determined by the $APM_{k0}$ signal:

$D_{APM_{k0}ind} = (G_{APM_{k0}}(d_a(t_a):d_b(t_b)) == 1)$ $Pos_{ideal}(D_{APM_{k0}ind}) = APM_{k0}(D_{APM_{k0}ind})$ In the above notation, $D_{APM_{k0}ind}$ refers to the time-point indices inside the gating window according to the $APM_{k0}$ signal over the sliding dosimetric window, whereas $G_{APM_{k0}}$ refers to the corresponding indices within the corresponding dosimetric window. The time-points $t_a$ and $t_b$ refer to the start and end times of the dosimetric window corresponding to the ideal machine scenario. In other words, the dosimetric window has been re-parameterised in terms of a temporal window. This may enable easier mapping between the window and parts of a treatment or stages of the respiratory cycle of the subject. The techniques described herein are applicable to a sliding window comprising a dosimetric window or comprising a temporal window.

Similarly, for the actual machine, the target was within the gating window, as determined by the $Pred_{k0}$ signal:

$D_{Pred_{k0}ind} = (G_{Pred_{k0}}(d_a(t_c):d_b(t_d)) == 1)$ $Pos_{actual}(D_{Pred_{k0}ind}) = APM_{k0}(D_{Pred_{k0}ind})$ Here the above notation $D_{Pred_{k0}ind}$ refers to the time-point indices where gating is triggered according to the $Pred_{k0}$ signal over the dosimetric window, whereas $G_{Pred_{k0}}$ refers to the corresponding indices within the corresponding dosimetric window. The time-points $t_c$ and $t_d$ refer to the start and end times of the dosimetric window of the actual machine scenario. In the case of perfect gating, the ideal and actual machine scenarios would be equivalent and $t_a = t_c$, $t_b = t_d$. However, due to imperfect gating, e.g. due to imperfect prediction modelling, the start and end times of $D_w$ are expected to correspond to different time-points.

Characterisation of the error between the ideal and actual scenarios, i.e. between calculations based on the measured and estimated target position signals, will now be considered. Positional statistics of the position values may be generated as follows:

$$Pos_{ideal\mu}(D_w) = \frac{1}{N_{D_w}} \sum_{d=1}^{D_w} (Pos_{ideal}(d))$$

$$Pos_{actual\mu}(D_w) = \frac{1}{N_{D_w}} \sum_{d=1}^{D_w} (Pos_{actual}(d))$$

$$Pos_{ideal\sigma}(D_w) = \sqrt{\frac{1}{N_{D_w}-1} \sum_{d=1}^{D_w} |Pos_{ideal}(d) - Pos_{ideal\mu}(D_w)|^2}$$

$$Pos_{actual\sigma}(D_w) = \sqrt{\frac{1}{N_{D_w}-1} \sum_{d=1}^{D_w} |Pos_{actual}(d) - Pos_{actual\mu}(D_w)|^2}$$

In the above expressions, $N_{D_w}$ is the number of samples in the dosimetric window. $Pos_{ideal\mu}$ is the mean of the positions ($Pos_{ideal}$) for the ideal machine, i.e. of the measured target position signals. $Pos_{actual\mu}$ is the mean of the positions ($Pos_{actual}$) for the actual machine, i.e. of the estimated target position signals. $Pos_{ideal\sigma}$ is the standard deviation of the positions ($Pos_{ideal}$) for the ideal machine, i.e. of the measured target position signals. $Pos_{actuate}$ is the standard deviation of the positions ($Pos_{actual}$) for the actual machine, i.e. of the estimated target position signals.

Since the above expressions are weighted by $N_{D_w}$, i.e. the number of samples in the dosimetric window, the data is weighted and focused on a particular part of a radiotherapy treatment. This may make the positional error more accurate for the purposes of determining when to interrupt treatment. In one example, the data may be weighted and focused on one delivery event (i.e. beam-hold release) of several seconds. In a second example, the data weighting may be higher, which enables the calculation to be performed over multiple separate delivery events, each lasting several seconds. When setting the $N_{D_w}$ parameter, a balance must be maintained between high amounts of noise (i.e. very low $N_{D_w}$) and use of stale data (i.e. very high $N_{D_w}$). For example, if $N_{D_w}$ is set too low, then the mean and standard deviations could be distorted by a drastic change in positional amplitude of one sample. This one sample this could, for instance, correspond to the first imaging sample acquiring during a deep inhale following a breath-hold.

In some examples, $N_{D_w}$ may equal the number of MUs delivered during two beam-hold release events, which may occur over a time duration corresponding to two slow respiratory cycles, each lasting up to 7.5 seconds. For a sinusoidal waveform played out over a duration of, for instance, 15 seconds and with a gating duty cycle of 20%, dose will only be delivered for 3 seconds of that duration. The positional data corresponding to when dose is delivered may be calculated from the waveform based on the chosen gating window. The positional data for the remaining 12 seconds may not be included in the calculation of the positional error since the position of the subject during beam-hold does not affect the average delivered dosimetric distribution. Utilising data obtained during beam-hold release events enables a dosimetrically-relevant positional error to be calculated.

In 3 seconds, based on a nominal dose rate of 450 MUmin$^{-1}$, the dose delivered is expected to be approximately 25 MUs. The weighting based on this value may be selected to provide an optimal balance between too small a period/dose, for which the statistics will be noisy, and too large a period/dose, for which the calculation will include out of date information that may no longer be a relevant or accurate indication of the pattern of movement of the subject. For example, if a period corresponding to a dose of 125 MUs were to be considered, then the positional statistics would be very smooth (i.e. almost no noise), but the data could be stale. This is important as the average position of the subject can drift during treatment. This drift may be captured by considering the 25 MUs dose but captured less well or missed by considering the 125 MUs dose.

As described herein, a positional error is calculated between a measured target position signal sampled at image acquisition times (i.e. with latency compensation) and an estimated target position signal. The positional error is calculated over a sliding window of a radiotherapy treatment. The sliding window may comprise a plurality of timepoints, which enables more accurate calculation of errors, rather than relying on individual timepoints which may comprise transient errors which could lead to inaccurate or inefficient treatments. The positional error calculated herein may thus be determined with a slight temporal delay, e.g. one frame behind, to incorporate the measured target position signal, once it is time-shifted to compensate for system latency, into the calculation. The positional error may be calculated over a treatment window, for example over a subset of a radiotherapy treatment session. The window may correspond to a selected period when the beam is delivered (i.e. to a beam-hold release period) or to a window corresponding to one or more respiratory cycles. This may enable the positional error to take into account particular parts of a treatment session for which accurate positioning of the target is particularly important (e.g. parts for which the beam is delivered), while disregarding other parts of the treatment session, for example during which no treatment is intended or delivered.

As described herein, the positional error is calculated, rather than merely estimated, inferred or considered probabilistically. This enables more robust control of the radiotherapy treatment in view of changeable target positions. The positional error may be described as a statistical error or an error in a position of the target. As described herein, the error that is calculated is a positional error. In other words, the error describes an error in an estimated location of the target relative to a measured location of the target. In other words, the error takes the form or is in the units of a distance. Therefore, the positional error calculated herein is based on real parameters directly relevant to the radiotherapy machine, the subject and the radiotherapy treatment, rather than merely considering abstract, dimensionless values. This facilitates improved control of the radiotherapy treatment through enabling more direct responses in terms of adjustment of the target/subject and/or of parts of the radiotherapy device.

The calculated positional error may be or include a mean error, i.e. a difference (for example an absolute difference) between the mean $Pos_{ideal\mu}$ of the measured target position signal and the mean $Pos_{actual\mu}$ of the estimated target position signal. As will be appreciated, this enables the positional error to take into account the difference between the average or centre-point of the measured and estimated target position signals, thereby providing an indication of the time-averaged separation between the measured and estimated target positions.

The calculated positional error may be or include a standard deviation error, i.e. a difference (for example an absolute difference) between the standard deviation $POS_{ideal\sigma}$ of the measured target position signal and the standard deviation $POS_{actual\sigma}$ of the estimated target position signal. As will be appreciated, this enables the positional error to take into account the relative spreads of the measured and estimated target position signals, thereby providing an indication of the time-averaged dispersion differences between the distributions of the measured and estimated target positions.

The calculated positional error may be or include other statistical metrics, such as the median, the mode, the variance, inter-quartile range, the range or percentiles.

Two signals each with peaks with identical shapes, with one shifted forward or backward in time relative to the other, may have the same standard deviation. Two signals each with peaks around the same centre-point, with one having a sharper or flatter form of peak, may have the same mean. The calculated positional error described herein may include a mean error and a standard deviation error. The calculated positional error described herein may include a difference, for example an absolute difference, between the mean $POS_{ideal\mu}$ of the measured target position signals and the mean $Pos_{actual\mu}$ of the estimated target position signals, and may include a difference, for example an absolute difference, between the standard deviation $POS_{ideal\sigma}$ of the measured target position signals and the standard deviation $POS_{actual\sigma}$ of the estimated target position signals. In other words, the difference in the means and the difference in the standard deviations may be combined in the calculation of the positional error by summation, multiplication, weighting, or any other function. This may provide a more accurate and reliable positional error and thereby more accurate and reliable control of the radiotherapy device through taking into account both the relative separations and relative spreads of the measured and estimated target position signals.

In particular, the mean ($\varepsilon_\mu$) and standard deviation ($\varepsilon_\sigma$) spatial positional errors may be defined as:

$$\varepsilon_\mu = |Pos_{ideal\mu} - Pos_{actual\mu}|$$

$$E6 = |Pos_{ideal\sigma} - Pos_{actual\sigma}|$$

The positional error may be defined as $\varepsilon_\mu + \varepsilon_\sigma$. The inventors have identified that this combination of the mean and standard deviation spatial positional errors is particularly suitable for characterising the deviations of the measured and estimated target position signals. In the sum of the mean and standard deviation spatial positional errors, the mean error may be multiplied by a weighting factor and/or the standard deviation error may be multiplied by a weighting factor. This may enable the operation of the radiotherapy device to be altered or continued with increased focus on either the centre-points or the spreads of the signals.

The positional error, calculated in one of the ways described above, may be compared to a threshold x. This threshold may be predefined based on one or more of previous measurements, simulations and decisions by a clinician. The threshold may be determined based on one or more of a particular location of a tumour, a particular profile of subject, a particular type of treatment being applied and a dose rate of the treatment. In some examples, the threshold may be varied during treatment to take into account time-varying machine parameters (for example the dose rate of treatment), or time-varying subject positions. As used herein, references to violating a threshold may be used to refer to exceeding a threshold. In a particular example, the following form of comparison may be used:

Treatment shall be altered if $(\varepsilon_\mu + \varepsilon_\sigma) > x$ mm over a sliding temporal window of y seconds.

This comparison may be referred to herein as a risk control measure (RCM). In some examples, the altering of the treatment may include interrupting, pausing or terminating the treatment. In some examples, the altering of the treatment may include altering, for example reducing, the dose rate of the treatment. In some examples, the altering of the treatment may include moving one or more of a radiation source, a leaf of a collimator or a patient positioning surface in dependence on the positional error. A computer-executable instruction may be generated, for example by a controller of the radiotherapy device, to alter the radiotherapy treatment in one or more of the ways described above.

In some examples, the techniques described herein may comprise determining whether the positional error violates a first threshold. If the positional error violates the first threshold, the radiotherapy treatment may be altered in response, for example by reducing the dose rate of the radiotherapy treatment and continuing the radiotherapy treatment at this reduced dose rate. If the positional error violates a second threshold, which may be larger than the first threshold, the radiotherapy treatment may be altered in response, for example by interrupting the radiotherapy treatment. This may enable the treatment to be continued with a lower dose rate if the positional error is slightly higher than desired but not dangerously high, and to be interrupted of the positional error is dangerously high. This may enable an improved optimisation between safety and efficiency of a radiotherapy treatment. In some examples, the continuation of the radiotherapy treatment at the lower dose rate may be limited to a particular time period or a particular delivered dose, following which the radiotherapy treatment may be interrupted in response if the positional error continues to violate the first threshold (but not necessarily the second threshold). If the radiotherapy treatment no longer violates the first threshold, the radiotherapy treatment may continue in accordance with a treatment plan, for example a pre-determined treatment plan. In other words, the radiotherapy treatment may continue with the higher/original dose rate.

Figure 4:
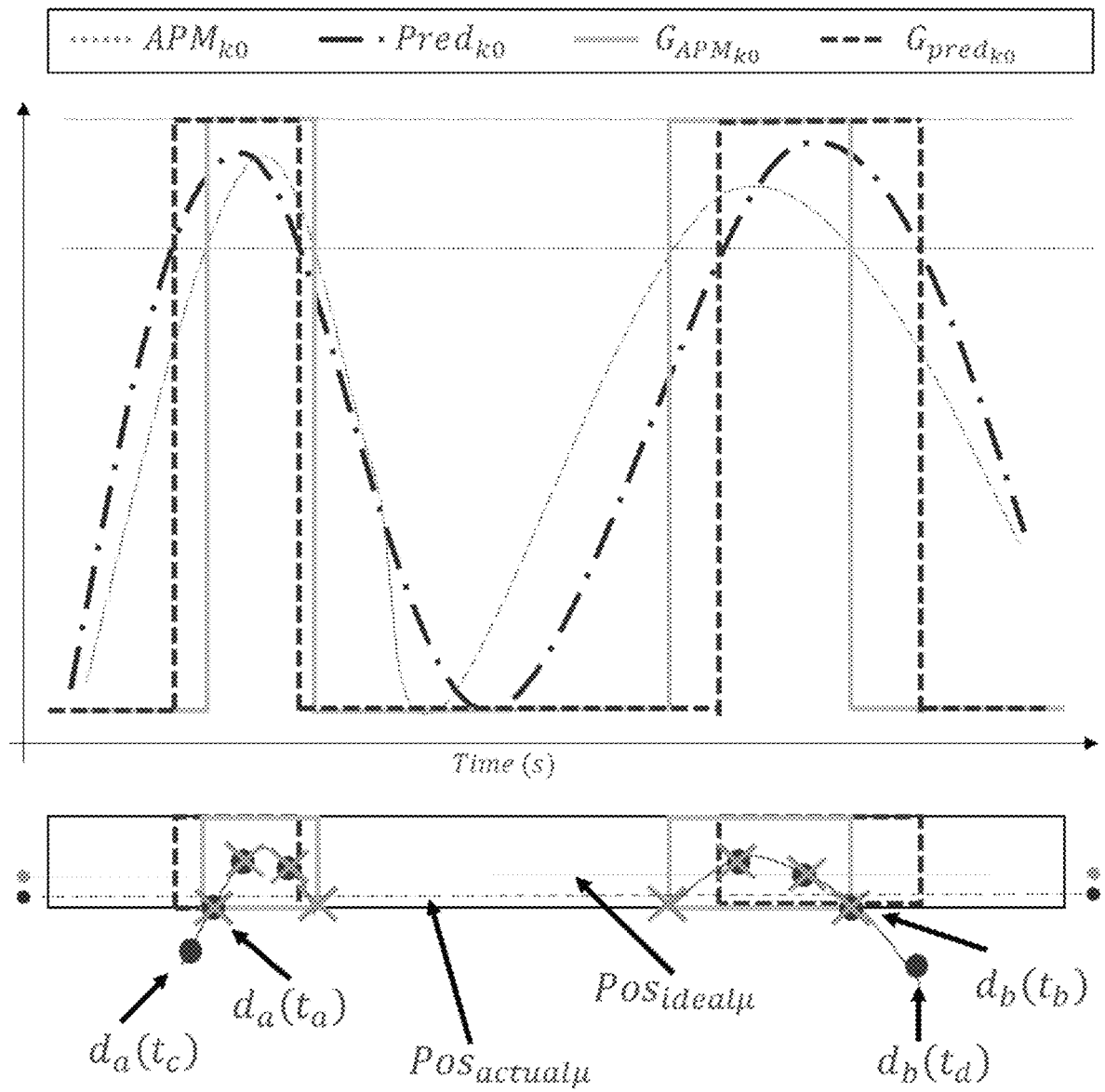
FIG. 4 depicts an example of position signals used for calculation of a positional error according to the present disclosure.

FIG. 4 shows example position signals which may be used for the spatial positional statistic calculation described above. Here, the sliding window $D_W$ has 8 MUs between $d_a$ and $d_b$. Crosses and dots symbolise MUs delivered according to the ideal ($G_{APM_{k0}}$) and actual ($G_{pred_{k0}}$) gated deliveries, respectively. Prediction errors mean that MUs are delivered at slightly different time points in the ideal and actual deliveries, which results in variations in the ideal and actual delivered dose distributions. For instance, in this example, the mean position of the actual dose delivery $Pos_{actual\mu}$ is lower than the mean position of the ideal dose delivery $Pos_{ideal\mu}$. The risk control measure described herein monitors the differences between the spatial positional statistics of the ideal and actual delivered dose distributions in order to determine more reliably whether treatment should be altered in response.

Figure 5A:
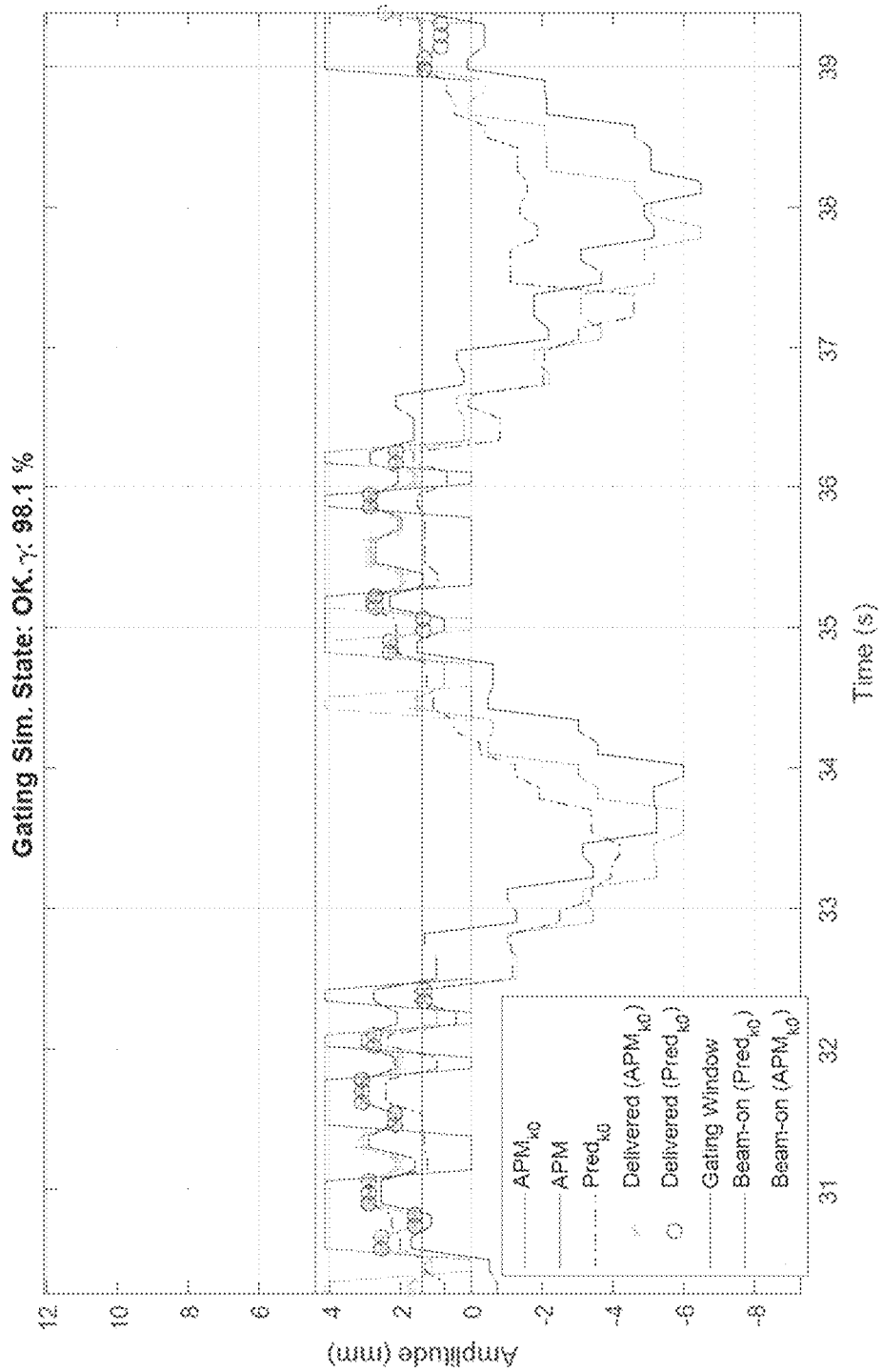
FIG. 5A depicts an example of position signals used for calculation of a positional error for a real subject waveform according to the present disclosure.
Figure 5B:
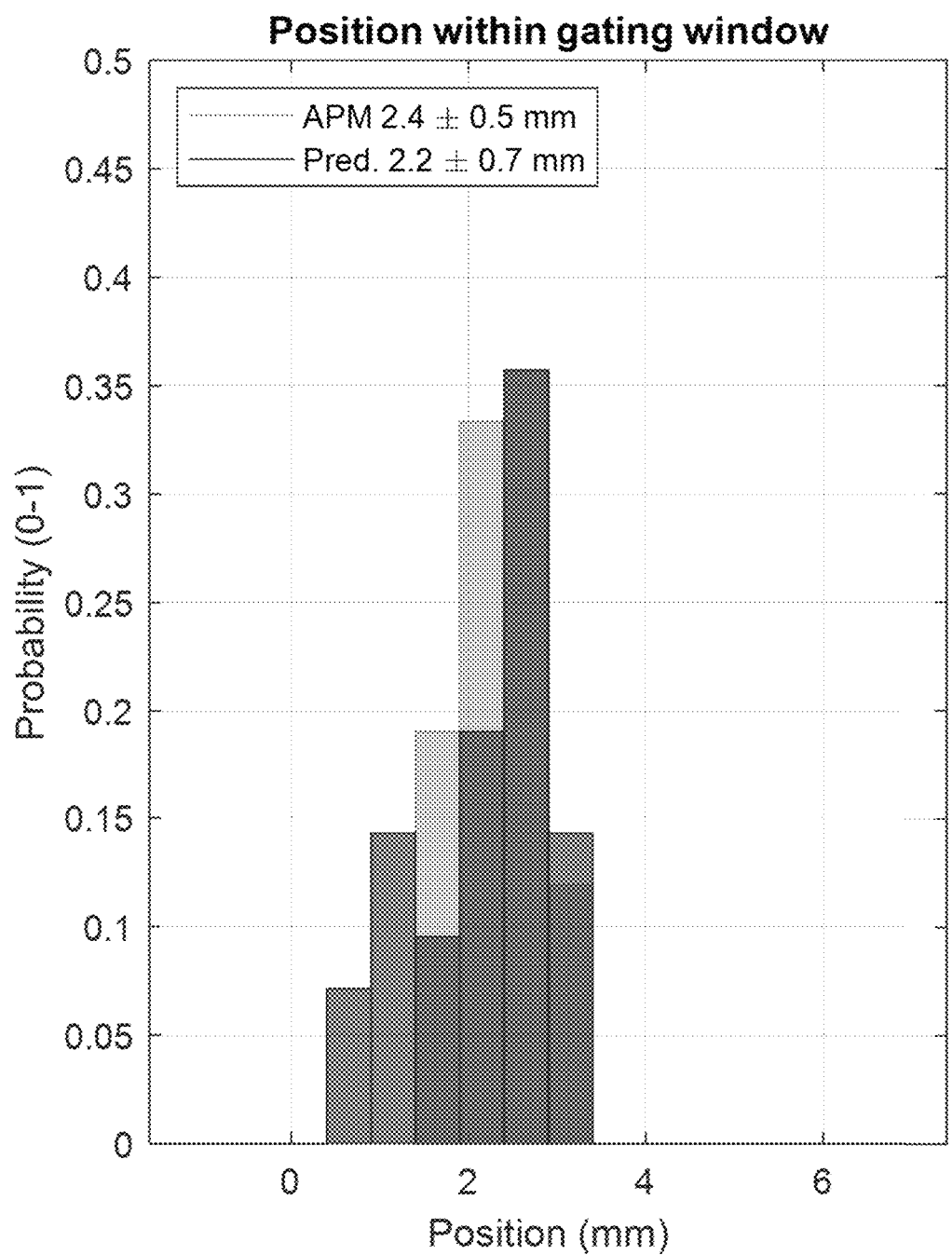
FIG. 5B depicts a variation between ideal and actual positional distributions according to the present disclosure.

FIG. 5A provides an additional example, for a real subject waveform, of the position signals used for the gating simulation and spatial positional statistics calculation. The plot shows an example gating simulation for a subject. As can be seen, the estimated target position signal varies relative to the measured target position signal, leading to discrepancies between the respective gating decisions taken based on these signals. Differences in gating between the ideal and actual machine are visible as differences between the $G_{APM_{k0}}$ and $G_{pred_{k0}}$ gating signals. This is manifested in a spatial positional error, which is depicted in FIG. 5B as a variation between the ideal and actual positional distributions.

A latch-based logic for implementing the risk control measure described herein will now be discussed. For a given sliding window, if the threshold set as part of the risk control measure is violated (e.g. if $(\varepsilon_\mu + \varepsilon_\sigma) > x$ mm), then the treatment delivery is altered, e.g. interrupted. Once treatment is altered, a counter may be programmed to begin. If the threshold is not subsequently violated for t seconds after the alteration, then treatment delivery may be resumed or continued in accordance with a treatment plan. If the threshold is again violated within the t seconds, then the counter may be reset to zero and begin counting again.

This latch-based logic avoids transitory behaviour whilst enabling the system to self-recover if the prediction accuracy improves. For instance, if the patient begins coughing unexpectedly during treatment delivery, then the prediction accuracy is expected to decrease, which may consequently trigger the latch, i.e. violate the threshold. If the patient finishes coughing, then the positional error should decrease to within tolerance and treatment will be permitted to resume or continue in accordance with a treatment plan. This provides an optimised balance between avoiding, one the one hand, resuming or continuing treatment too early following violation of the threshold in a potentially unsafe manner, and, on the other hand, allowing a transient event leading to temporary violation of the threshold to end an entire treatment session in an inefficient manner.

Figure 6:
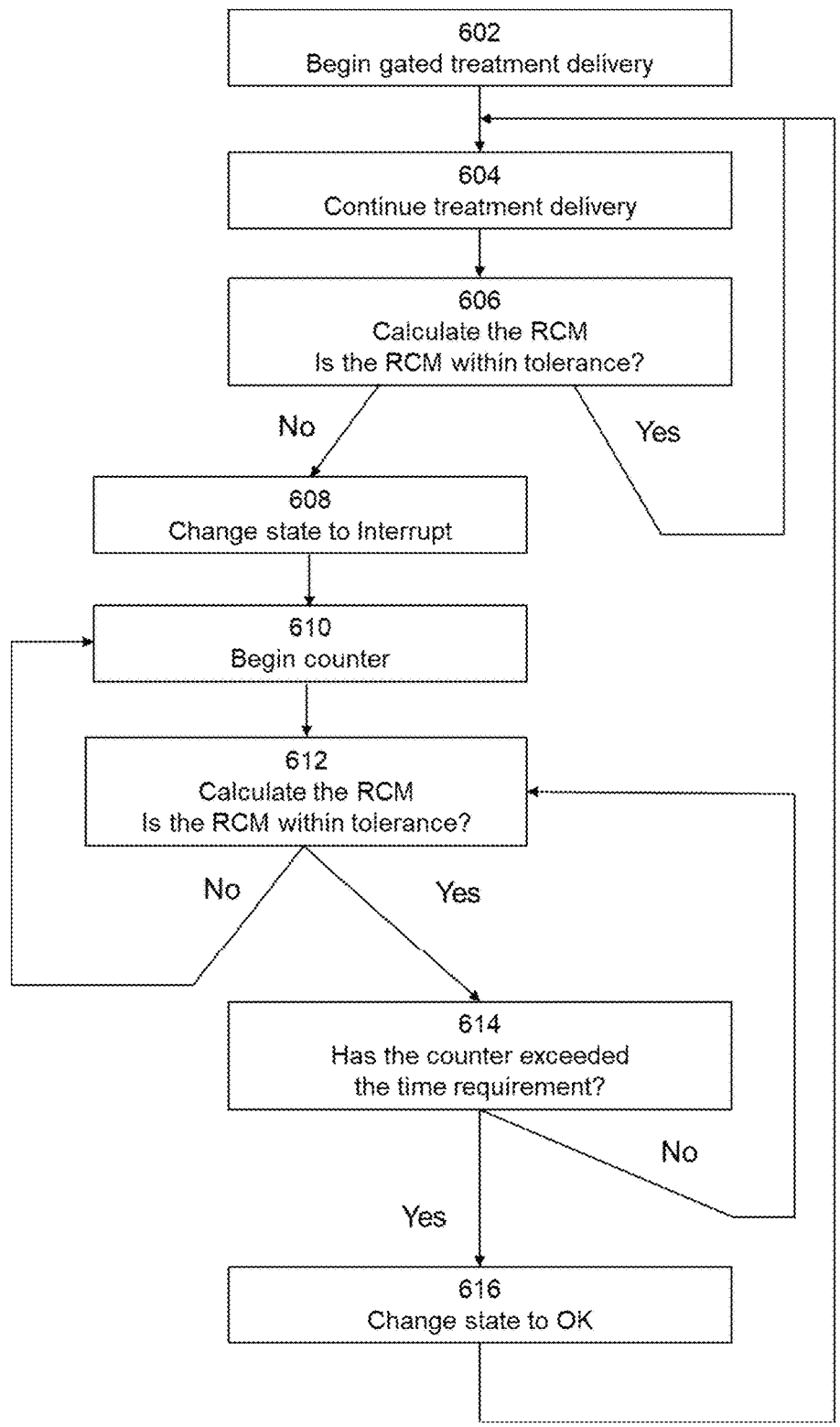
FIG. 6 depicts an example workflow for latch-based logic according to the present disclosure.

FIG. 6 shows an example workflow of the latch-based logic. The method of FIG. 6 may be implemented by the controller or control device described herein. While FIG. 6 shows an example in which a gated treatment delivery and interruption of the treatment are considered, it will be appreciated that the latch-based logic is applicable to other types of treatment delivery and/or to other responses to violation of a threshold.

At a step 602, a gated treatment delivery may begin. At a step 604, the treatment delivery may be continued.

At a step 606, the risk control measure (RCM), i.e. the positional error, may be calculated and it may be determined whether this violates a threshold, i.e. whether it is within tolerance. If it is within tolerance, then the method may return to step 604. If it is not within tolerance, then the method may continue to step 608, at which the treatment is interrupted through changing a state of a field in computer-executable instructions to Interrupt.

At a step 610, a counter may be begun. The counter may record how long it has been since the threshold was violated/ since the radiotherapy treatment was altered. At a step 612, the risk control measure (RCM), i.e. the positional error, may be calculated and it may be determined whether this violates a threshold, i.e. whether it is within tolerance. If it is not within tolerance, i.e. if it continues to violate the threshold, then the method may return to the step 610, at which the counter is begun, i.e. is reset to zero. If it is within tolerance, then the method may continue to step 614, at which it is determined whether the counter has exceeded a time requirement, i.e. a time threshold. If it has not been exceeded, then the method may return to step 612. If it has been exceeded, then the method may continue to step 616, at which a state of a field in computer-executable instructions may be set to OK. Following step 616, the method may return to step 604 at which the treatment may be resumed or continued in accordance with a treatment plan. One or more of the steps 604-616 may be repeated, for example a plurality of times, during the same or additional radiotherapy treatments.

Methods for relating the positional error and the threshold discussed above to dosimetric considerations will now be described. As described above, the positional error calculated and utilised herein is based on real parameters directly relevant to the radiotherapy machine, the subject and the radiotherapy treatment, rather than merely considering abstract, dimensionless values. In particular, comparing the positional error to a threshold determined through dosimetric analysis, as will be described below, enables safer and more efficient radiotherapy treatment through quantifying for which positional errors it is safe to continue radiotherapy treatment and for which positional errors radiotherapy treatment should be altered, e.g. interrupted.

Local Gamma ($\gamma$) analysis may be utilised to evaluate the efficacy of the RCM as a dose surrogate through the calculation of a gamma index:

$$\gamma(ref) = \mathrm{Argmin}_{eval}\left(\sqrt{\frac{(ref - eval)^2}{\Delta DTA^2} + \frac{(D_{ref}(ref) - D_{eval}(eval))^2}{\Delta D^2}}\right)$$

Above, ref and eval refer to spatial points in the reference (ideal) and evaluated (actual) dosimetric distributions. $\Delta DTA$ is the dose to agreement and $\Delta D$ is the dose difference. $D_{ref}$ and $D_{eval}$ represent the ideal and actual dosimetric distributions. The pass-rate ($\gamma_{pass}$) may be calculated as the percentage of points in $\gamma(ref)<1$. Various different Gamma criteria may be applied to capture desired accuracies, safety margins, anatomical locations of treatment, etc. As test examples, two separate sets of Gamma criteria are discussed below:
1) $\Delta D=3\%$, $\Delta DTA=2$ mm, Threshold=10%, pass-rate>90%.
2) $\Delta D=5\%$, $\Delta DTA=2$ mm, Threshold=10%, pass-rate>90%.

A simulation was implemented to perform Gamma analysis over a whole film by comparing the blurred dosimetric distributions obtained by:

Ideal machine/measured target position signals: delivering radiation to the square target, which has positions given by the $APM_{k0}$ signal, according to the ideal gating delivery scenario $G_{APM_{k0}}$.

Actual machine/estimated target position signals: delivering radiation to the square target, which has positions given by the $APM_{k0}$ signal, according to the actual gating delivery scenario $G_{Pred_{k0}}$.

Figure 7A:
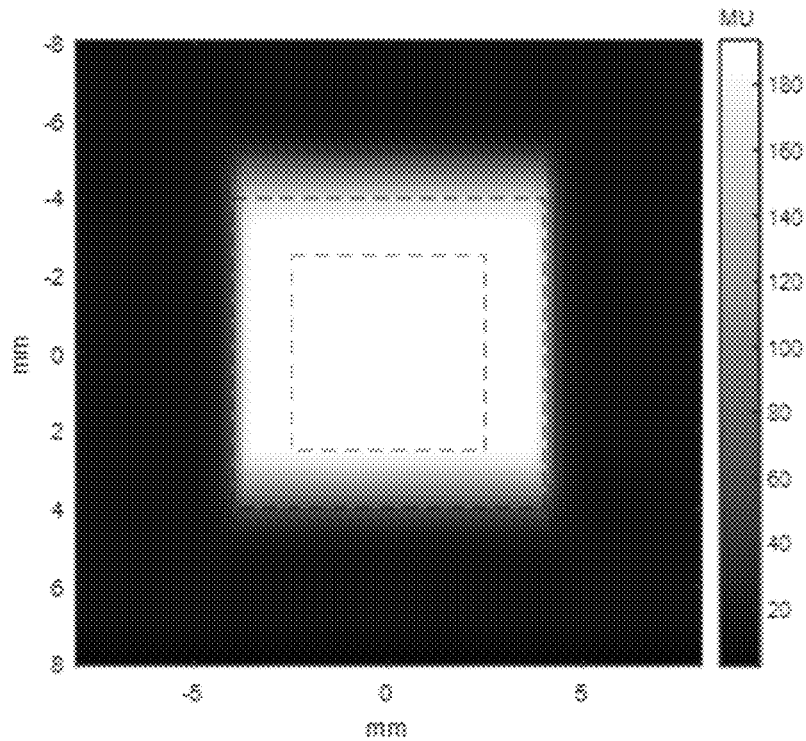
FIGS. 7A-C depict an example Gamma analysis according to the present disclosure.
Figure 7B:
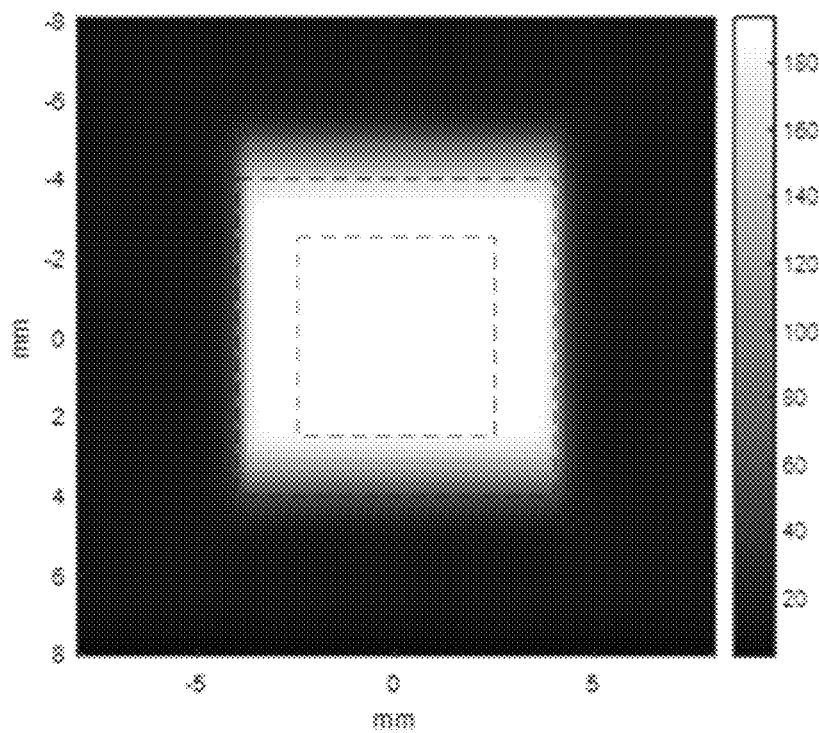
Figure 7C:
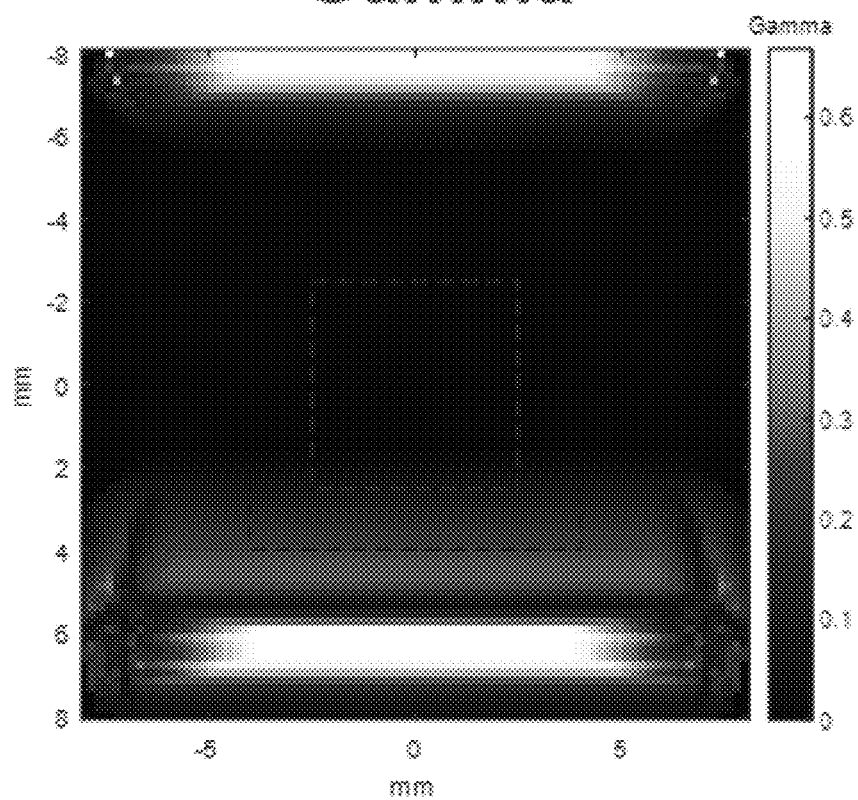

Dose delivered in the ideal and actual deliveries was the same. In such analysis, blurred distributions are expected due to the finite size of the gating window. FIG. 7 shows an example Gamma analysis. In particular, FIG. 7A corresponds to the ideal machine, i.e. to the measured target position signals. FIG. 7B corresponds to the actual machine, i.e. to the estimated target position signals. FIG. 7C displays the resulting Gamma score obtained by comparing the data associated with FIGS. 7A and 7B.

Pearson's r, i.e. Pearson's correlation co-efficient, was used to determine the correlation between the spatial positional errors ($\varepsilon_\mu$ and $\varepsilon_\sigma$) and the simulated $\gamma_{pass}$:

$$r_{\gamma_{pass}\varepsilon} = \frac{\mathrm{cov}(\gamma_{pass}, \varepsilon)}{\sigma_{\gamma_{pass}}\sigma_\varepsilon}$$

As the skilled person will be familiar with, Pearson's r provides a measure of linear correlation between two sets of data. Linear regression was applied to estimate the relationship (i.e. to calculate $x_1$, $x_2$ or $x_3$) between the simulated $\gamma_{pass}$ and the spatial positional errors:

$$\gamma_{pass1}=x_1\varepsilon_\mu+100$$

$$\gamma_{pass2}=x_2\varepsilon_\sigma+100$$

$$\gamma_{pass3}=x_3(\varepsilon_\mu+\varepsilon_\sigma)+100$$

In order to evaluate the accuracy of the calculated fit, the percentage error was calculated between the simulated $\gamma_{pass}$ and the pass-rates obtained from fitting: $\gamma_{pass1}$, $\gamma_{pass2}$ and $\gamma_{pass3}$.

Afterwards, for the fit with the lowest percentage error, obtained data comprising 16 subject trajectories was split into training and validation sets. The training set contained the first 75% of the data (subject waveforms 1 to 12) and the validation set contained the last 25% of the data (subject waveforms 13 to 16). Linear regression was independently repeated for the training and validation sets to verify the calculated fit.

Additionally, the fit with the lowest percentage error was applied to the positional error data calculated using a phantom waveform (comprising an additional set of obtained data). The percentage error between the simulated $\gamma_{pass}$ and the fitted gamma pass-rate was then determined.

The simulation parameters are listed in Table 1. The sliding dosimetric window $D_w$ was set as 25 MUs. This value was chosen since it is roughly equivalent to the expected dose delivered over 15 seconds, which is approximately the time required by two (very) slow respiratory cycles (7.5 seconds each). The 25 MUs value can be calculated based on the expected dose delivered (dose rate=450 MUmin$^{-1}$) under gating conditions ($G_{win}=0.2$) during 15 seconds:

$$D_{15_s}=(7.5 \text{ MUs}^{-1})(15 \text{ s})(0.2) \sim 25 \text{ MU}$$

TABLE 1

| Simulation parameters. Two simulations were performed with Gamma criteria a) and b). | |
|---|---|
| Parameter | Simulation |
| Waveform | 16 subject trajectories and 1 phantom trajectory |
| Horizon (ms) | 350 |
| Frame-rate (ms) | 175 |
| Tumour-size (mm) | 15 |
| Simulation time (s) (from each subject) | 30 |
| Sliding dosimetric window (MU) | 25 |
| Linac sampling time (ms) | 80 |

TABLE 1-continued

Simulation parameters. Two simulations were performed with Gamma criteria a) and b).

| Parameter | Simulation |
| --- | --- |
| Linac dose rate (MU/min) | 450 |
| Gating window (%) | 20 |
| Gamma criteria (Whole Film) | a) 3%, 2 mm, 10% threshold, 90% pass-rate |
|  | b) 5%, 2 mm, 10% threshold, 90% pass-rate |
| Margin [M] (mm) | M = G |

Table 2 displays the calculated fit, percentage fit error and correlation (Pearson's r) for the spatial positional statistics and chosen Gamma criteria. For both criteria, the combination $\varepsilon_\mu + \varepsilon_\sigma$ resulted in the highest correlation and lowest fit errors.

TABLE 2

Summarises the calculated fits, fitting errors and fit correlations. 100% of the subject data was used for fitting.

| Gamma criteria | Error metric | Fit | Fit Error (%) | Correlation (r) |
| --- | --- | --- | --- | --- |
| 3%, 2 mm | $\varepsilon_\mu$ | $\gamma_{pass} = -16.1\varepsilon_\mu + 100$ | 3.8 | −0.73 |
|  | $\varepsilon_\sigma$ | $\gamma_{pass} = -20.0\varepsilon_\sigma + 100$ | 2.7 | −0.88 |
|  | $\varepsilon_\mu + \varepsilon_\sigma$ | $\gamma_{pass} = -9.7(\varepsilon_\mu + \varepsilon_\sigma) + 100$ | 2.5 | −0.89 |
| 5%, 2 mm | $\varepsilon_\mu$ | $\gamma_{pass} = -13.4\varepsilon_\mu + 100$ | 3.5 | −0.76 |
|  | $\varepsilon_\sigma$ | $\gamma_{pass} = -16.1\varepsilon_\sigma + 100$ | 3.1 | −0.86 |
|  | $\varepsilon_\mu + \varepsilon_\sigma$ | $\gamma_{pass} = -8.0(\varepsilon_\mu + \varepsilon_\sigma) + 100$ | 3.0 | −0.90 |

Figure 8:
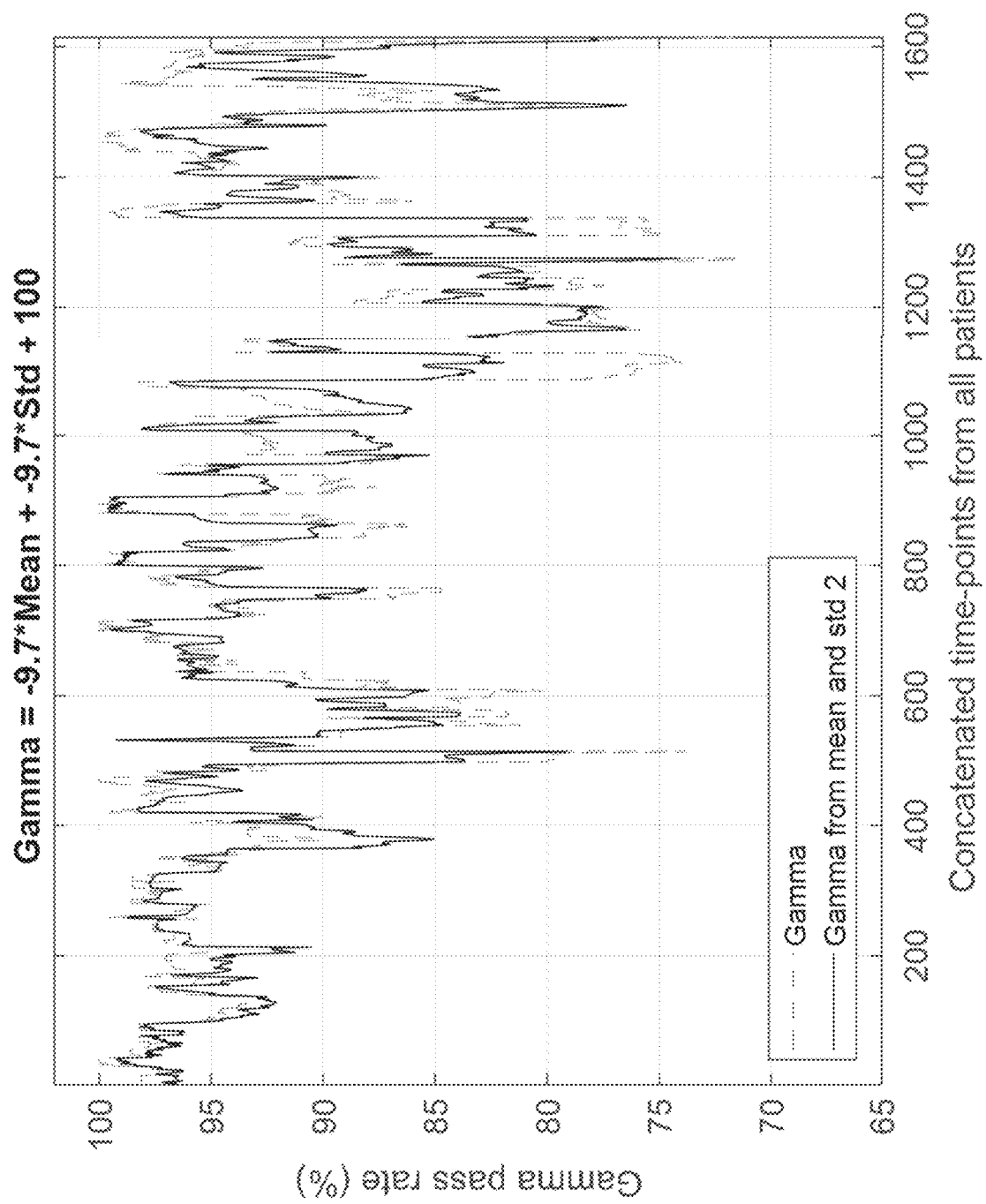
FIG. 8 depicts an example comparison between simulated and fitted Gamma pass rates according to the present disclosure.

FIG. 8 shows a pictorial view comparing the simulated and fitted $\gamma_{pass}$ for the $\varepsilon_\mu + \varepsilon_\sigma$ RCM. It displays an example comparison between the simulated (dashed-line) and fitted (solid-line: $\gamma_{pass} = -9.7(\varepsilon_\mu + \varepsilon_\sigma) + 100$) Gamma pass-rates for all concatenated subject data. Good agreement can be seen between features in the simulated and fitted Gamma pass-rates.

The fitting process for $\varepsilon_\mu + \varepsilon_\sigma$ was repeated using the first 12 patients and last 4 patients. For the 3%, 2 mm criteria, the fit found using 100% of the data (i.e. $x_3 = -9.7$) was similar to the fit found when using 75% (i.e. $x_3 = -10.0$) or 25% (i.e. $x_3 = -9.2$) of the data. A similar result was found for the 5%, 2 mm criteria. The fit parameters obtained using the test and validation data sets are provided in Table 3.

TABLE 3

Summarises the calculated fits, fitting errors and fit correlations. 75% (subjects 1 to 12) and 25% (subjects 13 to 16) of the subject data were used for fitting.

| Gamma criteria | Subject data | Fit | Fit Error (%) | Correlation (r) |
| --- | --- | --- | --- | --- |
| 3%, 2 mm | 1 to 12 | $\gamma_{pass} = -10.0(\varepsilon_\mu + \varepsilon_\sigma) + 100$ | 2.2 | −0.91 |
|  | 13 to 16 | $\gamma_{pass} = -9.2(\varepsilon_\mu + \varepsilon_\sigma) + 100$ | 3.5 | −0.87 |
| 5%, 2 mm | 1 to 12 | $\gamma_{pass} = -8.3(\varepsilon_\mu + \varepsilon_\sigma) + 100$ | 2.8 | −0.92 |
|  | 13 to 16 | $\gamma_{pass} = -7.5(\varepsilon_\mu + \varepsilon_\sigma) + 100$ | 3.8 | −0.87 |

The best linear fit ($\gamma_{pass} = -9.7(\varepsilon_\mu + \varepsilon_\sigma) + 100$) obtained for the 3%, 2 mm criteria was applied to the phantom test data. A very minor fit error (2.6%) was found. Similar results were obtained when applying the best linear fit ($\gamma_{pass} = -8.0(\varepsilon_\mu + \varepsilon_\sigma) + 100$) found for the 5%, 2 mm criteria (2.2% fit error).

The calculated fits outlined in Table 2 were interpreted using the two Gamma criteria listed above, with the aim of achieving $\gamma_{pass} = 90\%$.

1) 3%, 2 mm Criteria:

$90 > -9.7(\varepsilon_\mu + \varepsilon_\sigma) + 100$, rearranges and rounds to:

$(\varepsilon_\mu + \varepsilon_\sigma) < 1$ mm 2) 5%, 2 mm Criteria:

$90 > -8.0(\varepsilon_\mu + \varepsilon_\sigma) + 100$, rearranges and rounds to:

$(\varepsilon_\mu + \varepsilon_\sigma) < 1.3$ mm

Therefore, taking by way of non-limiting example the 1.0 mm value, the RCM may be formulated as:

Treatment shall be interrupted if $(\varepsilon_\mu + \varepsilon_\sigma) > 1.0$ mm over a sliding temporal window of 15 seconds.

OR:

Treatment shall be interrupted if the absolute mean error plus the absolute standard deviation error, calculated between the actual target position and APM signals (with or without prediction) during irradiation (over a sliding temporal window of 15 seconds), exceeds 1.0 mm.

According to calculations using alternative parameter values, or an alternative consideration of the risk associated with a treatment, the threshold x may be equal to 2.8 mm, i.e. treatment may be interrupted if the positional error is greater than 2.8 mm.

The above analysis has been provided in order to demonstrate the robust connection between the positional error and thresholds used and the impact on the subject in terms of delivered dose. It will be appreciated that the techniques described herein are applicable to other forms of positional error, other radiotherapy treatment schemes, other windows, other thresholds and/or other responses to violating a threshold.

Examples demonstrating the performance of the above-described techniques when applied to test waveforms will now be described. For the 3%, 2 mm Gamma criteria, simulated $\gamma_{pass}$ were <90% for 10 out of 11 tested irregular waveforms. Moreover, simulated $\gamma_{pass}$ were >90% for 4 out 5 stable cases. This demonstrates the expected behaviour of the RCM, i.e. that the RCM was violated for irregular waveforms and not violated for stable waveforms. In other words, the techniques described herein successfully alter treatment when irregular motion leads to substantial deviations from expected motion and significant dosimetric errors, and allow treatment to continue when motion is regular and dosimetric errors are acceptable.

Figure 9:
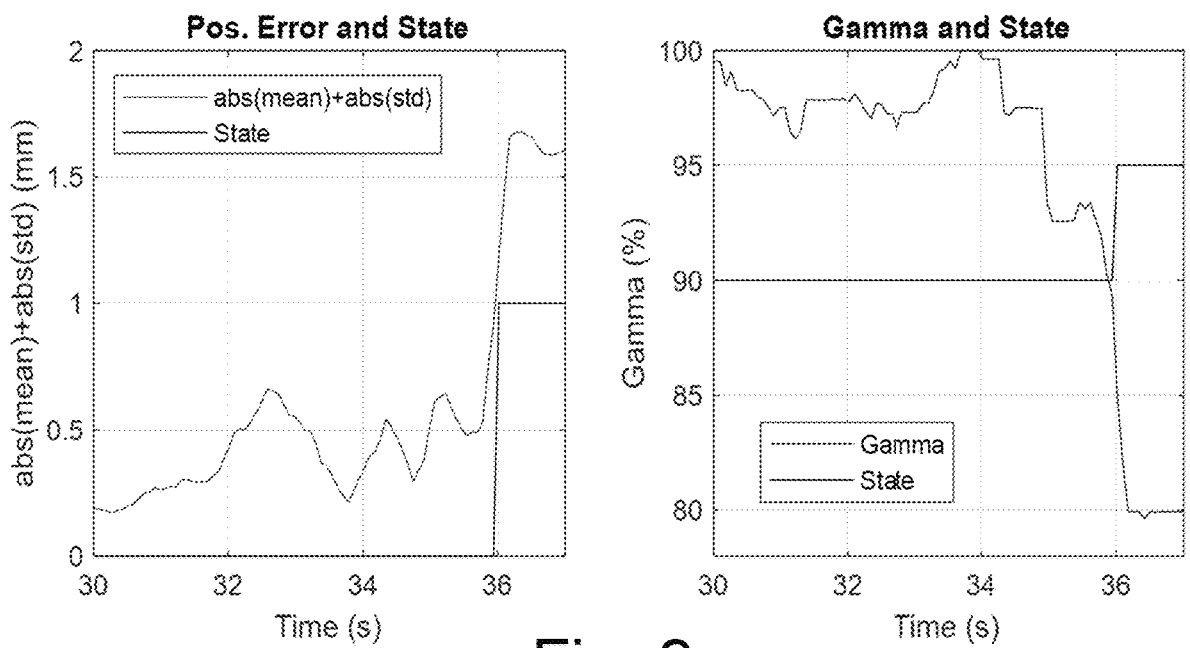
FIG. 9 depicts an example of the application of a risk control measure according to the present disclosure.

FIG. 9 shows an example of treatment being permitted by the RCM for a fraction of an analysed respiratory waveform. Altogether, this was the case for 6 out of the 11 irregular waveforms. As shown in FIG. 9, the beam state changes from OK (indicated by value 0 on the left-hand graph and value 90 on the right-hand graph) to Interrupt (indicated by value 1 on the left-hand graph and value 95 on the right-hand graph). The data for this waveform comes from a subject 5, who exhibited an irregular respiratory pattern. In this example, treatment is initially permitted between the treatment time of 30 to 36 seconds, but then interrupted between 36 and 37 seconds due to more irregular motion exhibited from approximately 36 seconds onwards.

Figure 10:
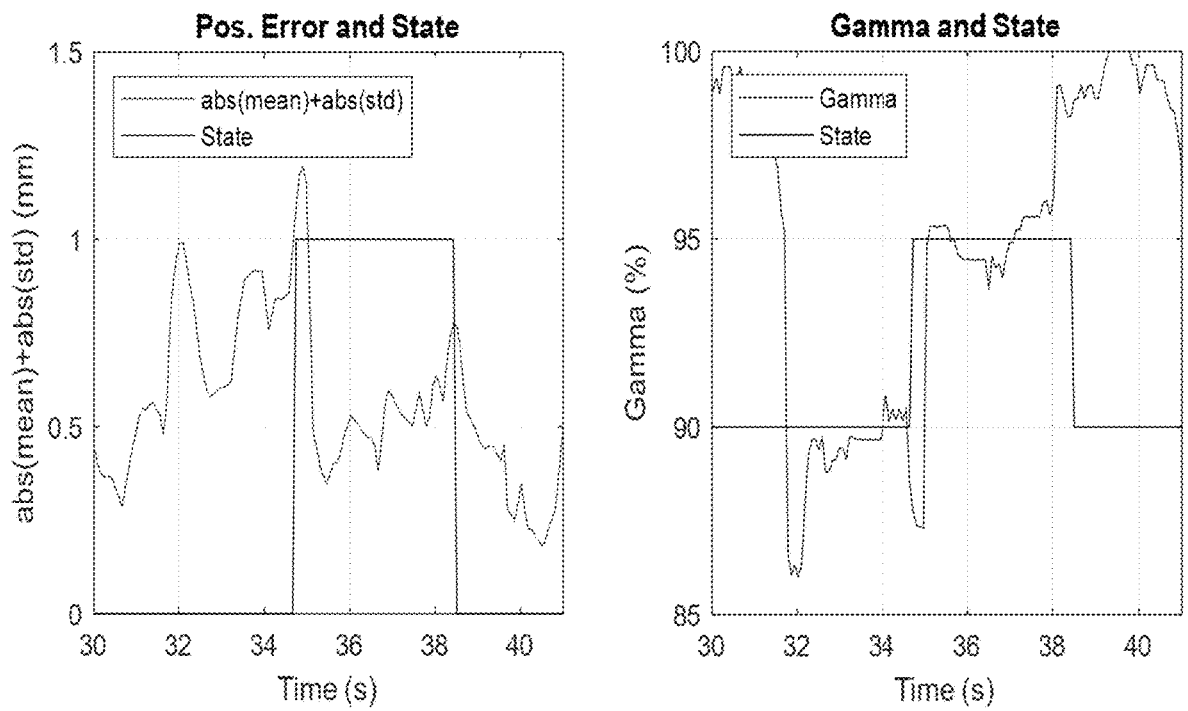
FIG. 10 depicts a further example of the application of a risk control measure according to the present disclosure.

FIG. 10 shows an example of the RCM enabling self-recovery. Altogether, this was the case for 2 out of the 11 irregular waveforms. FIG. 10 depicts a waveform with data from a subject 18, who exhibited an irregular respiratory pattern. The beam states are displayed as OK (indicated by value 0 on the left-hand graph and value 90 on the right-hand graph) or Interrupt (indicated by value 1 on the left-hand graph and value 95 on the right-hand graph). In this case, the positional error exceeds the set threshold at around 34.5-35 seconds, before quickly returning to an acceptable level. The RCM permits self-recovery around 38.5 seconds. This demonstrates action of the latch-based logic described above. The time counter may be begun at around 34.5-35 seconds and may exceed the time requirement at around 38.5 seconds, allowing treatment to continue. This enables a balance to be provided between self-recovery to provide efficient treatment and avoiding prematurely resuming treatment after an inappropriately short and possibly transitory period of more regular motion.

For the 5%, 2 mm Gamma criteria, simulated $\gamma_{pass}$ were <90% for 7 out of 11 tested irregular waveforms. Moreover, simulated $\gamma_{pass}$ were >90% for 4 out 5 stable cases. Similarly to the 3%, 2 mm Gamma criteria, the RCM was also violated for the majority of irregular waveforms. However, it is was more lenient since the RCM was violated for only 7 out of 11 irregular waveforms rather than 9 out of 11. This demonstrates that the techniques described herein can be tailored to respond with different levels of sensitivity to different levels of irregularity. For example, for some anatomical tumour locations there may be one or more organs at risk close to the target, which may indicate that only very small deviations are clinically acceptable. For other anatomical tumour locations, tolerance of slightly larger deviations may be clinically appropriate in view of providing improved efficiency of treatment. The criteria to be used may alternatively or in addition be based on the particular subject to be treated, for example their age, clinical vulnerability or medical history including pre-existing conditions or previous sessions of radiotherapy treatment.

The RCM described herein may be interpreted with reference to the van Herk margin recipe, where M, Σ, σ and $\sigma_p$ are used to represent the PTV margin, systematic errors, random errors and random errors due to the beam penumbra, respectively:

$$M = 2.5\Sigma + 1.28(\sqrt{\sigma^2 + \sigma_p^2} - \sigma_p)$$

Similarly to a PTV margin, the Gamma pass-rate is affected by systematic shifts (i.e. mean error $\varepsilon_\mu$) and random blurring errors ($\varepsilon_\sigma$).

The RCM was developed for two separate sets of Gamma criteria, resulting in two slightly different tolerances (1.0 and 1.3 mm). For the purpose of gating, the 5%, 2 mm criteria is sufficient for safety, based on which the corresponding tolerance of 1.3 mm may be utilised.

In the simulation described above, a sliding dosimetric window of 25 MUs was utilised to establish the relationship between dose (Gamma pass-rate) and spatial positional error. In practice, the dose window will fall at slightly different time-points for the $APM_{k0}$ and $Pred_{k0}$ signals. Because the dose to error relationship has been calculated, the RCM may instead be applied directly over a sliding temporal window of e.g. 15 seconds. The RCM can be implemented as soon as the data for the $APM_{k0}$ and $Pred_{k0}$ signals become available, which will be approximately $t_{0-5}$ seconds behind real-time.

As described herein, the measured target position signal may be determined by a position sensor of the radiotherapy device. The position sensor may be any suitable device configured to determine, monitor or measure a position of the subject or a part of the subject, for example a target such as a tumour. The position sensor may be an imaging device, such as an MR imaging device. The (MR) imaging device may determine three-dimensional spatial information for the subject/target. The position sensor may transmit the measured target position signal to the control device. The control device may receive the measured target position signal from the control device. The control device may select a subset of the data determined/transmitted by the position sensor to use as the measured target position signal. The control device may compensate the measured target position signal for a latency of the system, i.e. may re-sample the signal amplitude values at time-points where the images (e.g. the k-space centre points of MR images) were acquired.

In some examples, the control device may implement a prediction model to forecast the target position signal. The estimated target position signal may be based on data transmitted from the position sensor to the control device. The estimated target position signal may be determined based on previous timepoints of the data transmitted by the position sensor, for example those up to and including a current timepoint minus a latency of the system. In some examples, the control device may receive the estimated target position signal from another device to which it is communicatively coupled. In some examples, the control device may directly use the measured data from the position sensor as the estimated target position signal without compensating for system latency.

The control device calculates, for a sliding window of a radiotherapy treatment, a positional error between the measured target position signal re-sampled to compensate for the system latency and the estimated target position signal. The control device may re-calculate the position error at each timepoint, but the implementation of the sliding window may cause one previous timepoint (at the start of the window) to be excluded from the calculation each time a new (current) timepoint is included in the calculation.

The control device may compare the positional error to a threshold. The control device may perform this comparison each time the positional error is calculated, i.e. for every timepoint. The control device may determine that the positional error violates, e.g. exceeds, the threshold. In response to this determination, the control device generates a computer-executable instruction configured to alter the radiotherapy treatment.

The control device may transmit the computer-executable instruction to one or more components of the radiotherapy device, and these one or more components may alter, e.g. interrupt, treatment. The control device may transmit the computer-executable instruction to the radiation source, which may cause the radiation source to halt, gate or interrupt treatment by stopping generation or emission of a treatment beam. Alternatively, the computer-executable instruction may cause the radiation source to reduce the dose rate of the treatment beam or may cause the radiation source to move to a new location. The control device may transmit the computer-executable instruction to collimator, e.g. a multi-leaf collimator, which may cause the collimator to move one or more beam-shaping components, e.g. one or more leaves, of the collimator. The control device may transmit the computer-executable instruction to a patient positioning surface, which may cause the patient positioning surface to move to a new position through translation and/or rotation. The reduction of the dose rate and/or the movement of the radiation source/one or more beam-shaping components/patient positioning surface, may be dependent on the positional error. For example, if the control device calculates a larger positional error, it may generate (and transmit) a computer-executable instruction that causes the radiation source to reduce the dose rate by a larger amount. In some examples, the control device may generate (and transmit) multiple computer-executable instructions and send each of these to different respective components of the radiotherapy device.

In the examples of the techniques described herein set out above, prediction of the motion of the subject has been focused on. However, the techniques described herein are not limited to cases involving prediction. For the non-prediction case, the RCM could compare the behaviour of an ideal machine, with no latency, to the behaviour of the actual machine with latency and no prediction latency compensation. Mathematically, this would be possible by keeping the definition of the ideal machine the same and re-defining the actual machine based on the APM signal:

Ideal machine (corresponding to the measured target position signal): the target was within the gating window, as determined by the $APM_{k0}$ signal:

$$D_{APM_{k0}ind} = (G_{APM_{k0}}(d_a(t_a):d_b(t_b))-1)$$

$$Pos_{ideal}(D_{APM_{k0}ind}) = APM_{k0}(D_{APM_{k0}ind})$$

Actual machine (corresponding to the estimated target position signal): the target was within the gating window, as determined by the APM signal:

$$D_{APMind} = (G_{APM}(d_a(t_c):d_b(t_d)) = 1)$$

$$Pos_{actual}(D_{APMind}) = APM(D_{APMind})$$

In this case, the estimated target position signal is 'estimated' in that it provides an indication of where the target is expected to actually be located based on information that is out of date by the system latency. In other words, the position is 'estimated' in that the previously measured location of the subject is taken as the current position. In this case, the techniques described herein can be used to quantify and monitor the positional error that arises due to the system latency itself. It may be desirable to operate without a prediction model but rather based on the out of date measured positions for situations in which the system latency is particularly small or the positions are particularly stable, for example during breath hold or prostate treatments.

In some examples, if the target is undergoing generally periodic motion, such as that due to respiration, the estimated target position signal may be predicted based on recent position measurements (provided by the measured target position signal). In some examples, if the target is not undergoing generally periodic motion, such as for a breath-hold, head and neck or prostate treatment, the most recent measured position (provided by the measured target position signal), which will be out of date by the system latency, can be used as the estimated target position signal.

In the examples of the techniques described herein set out above, application of the RCM to gated treatments has been focused on. However, the techniques described herein are not limited to cases involving gating. For example, the techniques described herein may be applied to tracked deliveries. For tracked deliveries, the system is able to irradiate for any position of the respiratory cycle. Moreover, unlike gating where dose is delivered to the centre of a static pre-defined window, in tracked treatments, dose is delivered to the moving target position. Tracked treatments may be considered as gated treatments, except that the centre of the gating window moves with the tumour trajectory. For tracked deliveries, the behaviour of the ideal and actual machines may be written as:

Ideal machine (corresponding to the measured target position signal): radiation is delivered to the target position, over a time window $t_a$: $t_b$, as determined by the $APM_{k0}$ signal:

$$Pos_{ideal}(t_a:t_b) = APM_{k0}(t_a:t_b)$$

Actual machine (corresponding to the estimated target position signal): radiation is delivered to the target position, over a time window $t_a$: $t_b$, as determined by the $Pred_{k0}$ signal:

$$Pos_{actual}(t_a:t_b) = Pred_{k0}(t_a:t_b)$$

The RCM developed for gating may be similarly implemented for tracking by comparing the mean and standard deviation errors:

$$\varepsilon_\mu = |Pos_{ideal\mu} - Pos_{actual\mu}|$$

$$\varepsilon_\sigma = |Pos_{ideal\sigma} - Pos_{actual\sigma}|$$

In one non-limiting example, the RCM may be implemented by considering tracked treatments as dynamic gated treatments. In other words, where the centre of the gating window follows the target position. For slow-moving targets, the tracking and gating RCM implementations are similar, since the gating window centre position is approximately static. For fast moving targets, the tracked RCM may be similarly implemented as per the gating scenario, except using a smaller time window $t_a$: $t_b$. In some examples, $t_a$: $t_b$ may be between 350 ms to 2000 ms.

Figure 11:
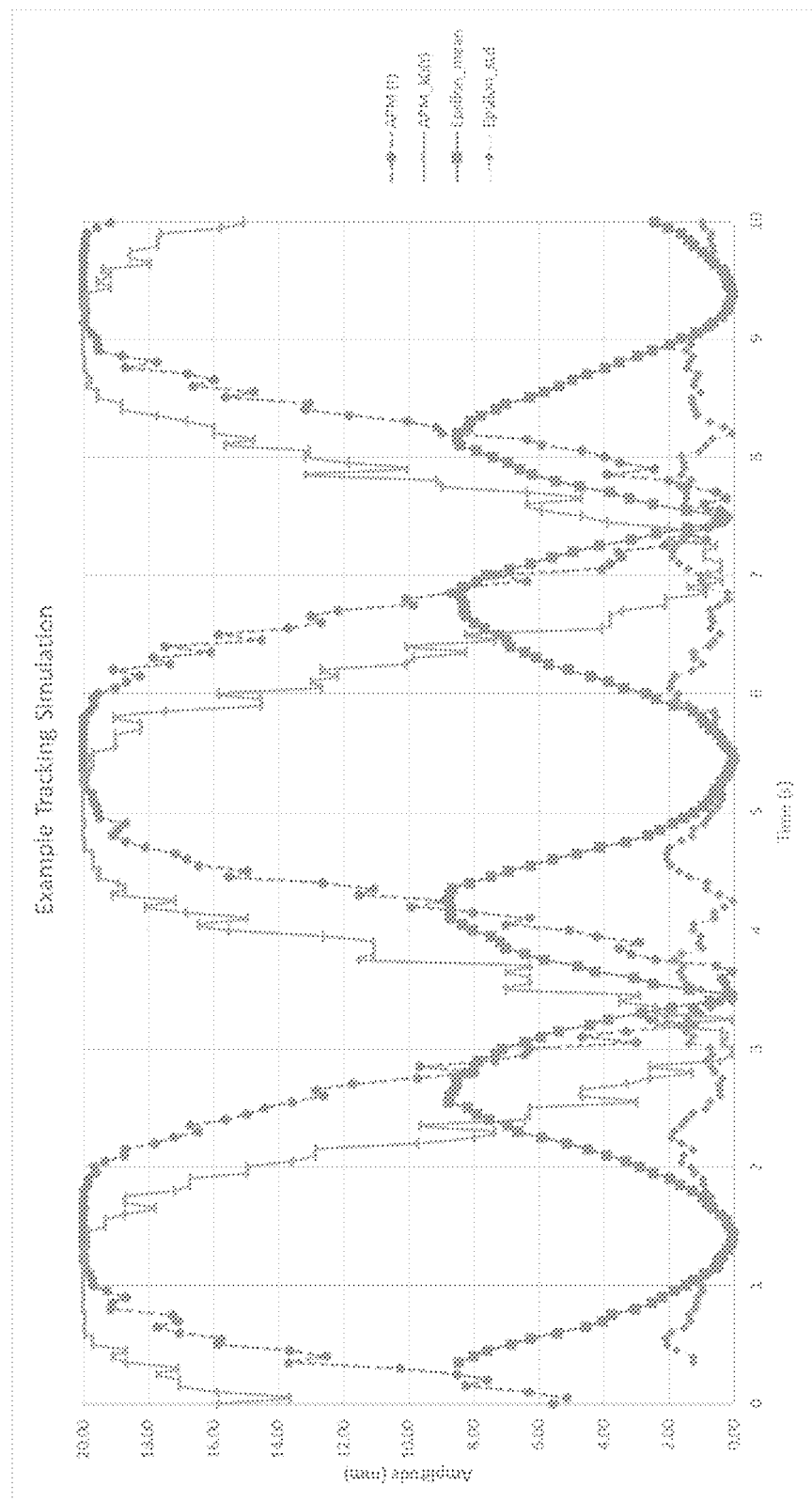
FIG. 11 depicts an example of the application of a risk control measure to tumour tracking according to the present disclosure.

FIG. 11 shows an example of the RCM as applied to tumour tracking. Here, the device is assumed to be delivering over the entire dose window (approx. 10 seconds). In this illustrative example, the APM signal is used in place of the prediction signal. Furthermore, the window $t_a$: $t_b$ was chosen as 350 ms. In FIG. 11, the $\varepsilon_\mu$ value increases when there are large differences between the APM and $APM_{k0}$ signals and decreases when the differences are reduced. A large value in the E value corresponds to a systematic shift in the dose over the time $t_a$:$t_b$. The $\varepsilon_\sigma$ value varies with the random noise exhibited by both signals. The $\varepsilon_\sigma$ parameter would capture random shifts in the dose distribution delivered between $t_a$: $t_b$ due to system latency.

Alternatively, for tracked deliveries, the previous values of the estimated position (i.e. values used by the gating algorithm) may be compared with the latency compensated 'measured position' to give an error. The statistics of the distribution of this error provide information about how the system latency affects the accuracy of the delivered dose. The average value of this error will correspond to a systematic shift in the delivered dose and therefore should have a tight tolerance. The variation or standard deviation of this error will have the effect of a random shift in the dose distribution. The delivered dose is a convolution of the probability distribution function of the error and the ideal dose distribution. As the ideal dose distribution varies slowly this variation can be allowed to be much bigger than the systematic error limit. Therefore, in the case of tracked deliveries, the statistics (e.g. taking of the mean and standard deviation) may instead be applied after the difference is taken and not independently as described for gating. As such, for tracked deliveries, the monitoring may not compare the distributions of the position between ideal and effective (measured and estimated), but rather ideal vs. actual position differences distribution (latency-compensated measured vs. estimated position differences distribution).

In some examples described herein, error checking can be applied using continuous dose calculation. The time matched measured position can be used when calculating the dose from the actual machine delivery parameters. In this way, the actual machine delivery parameters would include any errors arising from the system latency whereas the time matched measured position would not. Therefore, the accumulated dose will inform the user of the actual dosimetric effect of the latency and any other errors. The resulting dose distribution can then be compared against the physician's intent for this patient. This method could be used for either gating or tracking.

As used herein, when a position is referred to, this may refer to a position in 1D along a one-dimensional axis or may refer to a position in 2D with two spatial co-ordinates or a position in 3D with three spatial co-ordinates. For example, the measured target position signal and/or the estimated target position signal may describe a position in 1D, 2D or 3D. The positional error may describe the difference between the measured target position signal and the estimated target position signal in 1D, 2D or 3D. In some examples involving 2D or 3D measured and estimated target position signals, the positional error may be calculated as a vector between the measured and estimated target position signals. In some examples, a combined positional error may be calculated by summing the separately calculated positional errors for two or three dimensions.

The risk control measure may be calculated through consideration of one or more of the superior-inferior, anterior-posterior and medial-lateral dimensions. For the purposes of ease of understanding, in the frame of a human subject in a treatment position, these may be considered as extending respectively between the head and feet of the subject, into and out of the chest of the subject, and from the centre of the subject to the left-hand or right-hand side of the subject.

The positional statistics may be separately calculated for one or more dimensions, for instance the medial-lateral, anterior-posterior and superior-inferior dimensions. If the positional error violates a threshold for the superior-inferior threshold, anterior-posterior threshold or medial-lateral threshold, then the radiotherapy treatment may be altered in response. Alternatively, if the combined positional error for the superior-inferior, medial-lateral and anterior-posterior dimensions violates a combined threshold, the radiotherapy treatment may be altered in response. Treatment may be altered for example by interruption or by reducing the dose rate of the radiotherapy treatment and continuing the radiotherapy treatment at this reduced dose rate.

The mean error $\varepsilon_{\mu SI}$ for the superior-inferior dimension may be calculated. The standard deviation error $\varepsilon_{oSI}$ for the superior-inferior dimension may be calculated. The positional error for the superior-inferior dimension may be calculated and may be or include $\varepsilon_{\mu SI}$ and may be or include $\varepsilon_{oSI}$. The positional error for the superior-inferior dimension may be the sum of $\varepsilon_{\mu SI}$ and $\varepsilon_{oSI}$. The mean error $\varepsilon_{\mu AP}$ for the anterior-posterior dimension may be calculated. The standard deviation error $\varepsilon_{oAP}$ for the anterior-posterior dimension may be calculated. The positional error for the anterior-posterior dimension may be calculated and may be or include $\varepsilon_{\mu AP}$ and may be or include $\varepsilon_{oAP}$. The positional error for the anterior-posterior dimension may be the sum of $\varepsilon_{\mu AP}$ and $\varepsilon_{oAP}$. The mean error $\varepsilon_{\mu ML}$ for the medial-lateral dimension may be calculated. The standard deviation error $\varepsilon_{oML}$ for the medial-lateral dimension may be calculated. The positional error for the medial-lateral dimension may be calculated and may be or include $\varepsilon_{\mu ML}$ and may be or include $\varepsilon_{oML}$. The positional error for the medial-lateral dimension may be the sum of $\varepsilon_{\mu ML}$ and $\varepsilon_{oML}$.

One or more of the following risk control measures may be used:

The beam shall be held if $(\varepsilon_{\mu SI}+\varepsilon_{oSI})>x$ mm over a sliding temporal window of 15 seconds.

The beam shall be held if $(\varepsilon_{\mu AP}+\varepsilon_{oAP})>x$ mm over a sliding temporal window of 15 seconds.

The beam shall be held if $(\varepsilon_{\mu ML}+\varepsilon_{oML})>x$ mm over a sliding temporal window of 15 seconds.

The beam shall be held if $(\varepsilon_{\mu SI}+\varepsilon_{oSI})+(\varepsilon_{\mu AP}+\varepsilon_{oAP})+(\varepsilon_{\mu ML}+\varepsilon_{oML})>y$ mm over a sliding temporal window of 15 seconds.

For the combined positional error considered above in which the contributions from the different dimensions are summed, the combination may alternatively involve summing the respective positional errors for only two of the dimensions (i.e. for any two of the dimensions).

A threshold x of 2.8 mm, 1.3 mm, 1.0 mm, or any other suitable value, may be used. The threshold may be approximately 2.8 mm, or approximately 1.3 mm, or approximately 1.0 mm. The threshold x may be selected or calculated based on a suitable level of risk for a treatment. The combined threshold y may be the same as or different to the threshold x. The combined threshold y (also referred to as a multidimensional threshold or a joint threshold or a collective threshold) may be set to be larger than the threshold x to take into account the summing of the positional errors associated with the different spatial dimensions. In one example, the threshold y may be 3.0 mm, though any other suitable value may be used.

It will be understood that these risk control measures are presented by way of non-limiting example. In some examples, different thresholds may be used. In some examples, different lengths of temporal window may be used. In some examples, the risk control measure for one or more of the dimensions may have a different threshold and/or a different sliding window to the risk control measure for one or more of the other dimensions. For example, this may enable increased sensitivity to a positional error along a particular axis or in a particular direction to be accounted for through setting a smaller threshold. The setting of these one or more thresholds may be based on a shape and/or dimensions and/or anatomical location of a target region, for example a tumour. The setting of these one or more thresholds may be based on a shape and/or dimensions and/or anatomical location of an organ at risk.

In the above discussion, the definitions of the different signals are generally based on the timing framework as described in relation to FIG. 2A. According to this timing framework, a measured signal received by a controller at a current time T does not give the 'true' position at the current time T because the system latency means that the measured signal is out of date by the system latency. This measured signal is therefore re-sampled such that it gives the 'true' positions at the correct times. The estimated signal can be based on this re-sampled measured signal. For example, the estimated signal can comprise a position prediction for the current time T based on the re-sampled measured signal. The re-sampled measured signal gives the 'true' positions at the correct times, but, due to the system latency, cannot provide the 'true' position at the current time T. The estimated signal provides an estimation, e.g. a prediction, of this 'true' position at the current time T. The techniques described herein evaluate the accuracy of this estimation/prediction, i.e. through calculating a position error between the signals for a sliding window of a radiotherapy treatment.

The techniques described herein are not limited to the timing framework described above. It will be appreciated that these techniques may be self-consistently applied based on various different definitions of the signals. For example, the measured signal may be defined or parameterized based on the time of acquisition rather than based on the time it is received by the controller. The measured signal may be time-stamped by the anatomical motion capture device. In this case, re-sampling of the measured signal is not needed. The measured signal received by the controller at current time T gives the 'true' position at corresponding time points (though the most recent time point of the measured signal is in the past by the system latency). Where such a definition of the measured signal is used, the estimated signal may be based on previous values of the measured signal. In other words, the most recent value of the measured signal may be compared to an estimated signal calculated based on a value of the measured signal which is out of date with respect to the most recent value of the measured signal by the system latency. The estimated signal may be described as being sampled at a previous time to compensate for system latency. The estimated signal and the measured signal may be time-matched based on the system latency. In other words, the error calculation techniques described herein may be applied when an actual measurement is acquired the time of which matches the time of the estimated signal/the signal used by the gating algorithm.

The disclosure comprises a computer-implemented method comprising: calculating, for a sliding window of a radiotherapy treatment, a positional error between: a measured target position signal with latency compensation; and a predicted target position signal; and generating a computer-executable instruction configured to alter the radiotherapy treatment in response to the positional error violating a threshold.

The disclosure comprises a computer-implemented method comprising: calculating, for a sliding window of a radiotherapy treatment, a positional error between: a measured target position signal time stamped by the anatomical motion capture device; and an effective target position signal time re-sampled to compensate for system latency; and generating a computer-executable instruction configured to alter the radiotherapy treatment in response to the positional error violating a threshold. The effective target position signal may be constrained by inhibiting the target irradiation based on the latency uncompensated measured target position, or the effective target position signal may be constrained by inhibiting the target irradiation based on a predicted target position. The effective target position signal may be shaped by shifting the irradiation beam aperture toward the latency uncompensated measured target position, or the effective target position signal may be shaped by shifting the irradiation beam aperture toward a predicted target position.

The disclosure comprises a computer-implemented method comprising: calculating, for a sliding window of a radiotherapy treatment, a positional error between: a measured target position signal with latency compensation; and a measured target position signal; and generating a computer-executable instruction configured to alter the radiotherapy treatment in response to the positional error violating a threshold.

The disclosure comprises a control device configured to be communicatively coupled to a radiation source of a radiotherapy device and a position sensor of the radiotherapy device, the control device comprising a processor and computer-executable instructions which, when executed by the processor, cause the control device to: calculate, for a sliding window of a radiotherapy treatment, a positional error between: a measured target position with latency compensation and a measured target position; and generate a computer-executable instruction configured to alter the radiotherapy treatment in response to the positional error violating a threshold.

Where a measured target position signal determined from a series of images and sampled at the acquisition times of the images is referred to herein, this may be considered to be a measured target position signal with latency compensation, a measured target position signal time-shifted to compensate for system latency, a latency-compensated measured target position signal, or a measured target position signal (re-)sampled at k-space (centre) acquisition times. The data points for the target position may be taken/sampled at the timepoints at which the image was acquired by the position sensor/imaging apparatus (e.g. an MR imaging apparatus) rather than at the timepoints of the raw APM output signal with system latency. The 'latency compensation' of the measured target position signal may indicate what the measured position would have been at the time of the particular predicted position that is being tested by the risk control measure described herein.

Where an estimated target position signal is referred to herein, this may be considered to be a predicted target position signal, an extrapolated position signal, a measured target position signal not compensated for system latency, a gating decision target position signal or a target position signal used/usable for determining whether to gate a radiotherapy beam. The prediction/extrapolation of positions can be from duplication of the last measured data point, or prediction based on one or more data points, or determined via AI-based inference, etc.

Any of the techniques described above in the context of risk control measures are applicable individually or in combination to the two-dimensional risk control measures, and/or to the three-dimensional risk control measures. For example, such techniques may be applied to the risk control measure along one or more of the dimensions as described above, and/or may be applied to the combined risk control measure, where the contributions of the different dimensions are summed, as described above.

While the methods disclosed herein are presented in a certain sequential order, this should not be taken to limit the methods to the orders presented. One or more of the method steps may be omitted or rearranged. The various steps may be performed in different orders. Various steps may be performed at the same time or substantially the same time. Herein, references to events occurring substantially at the same time may refer to events at least partially overlapping in time and/or events occurring at the same time within measurement uncertainties.

Figure 12:
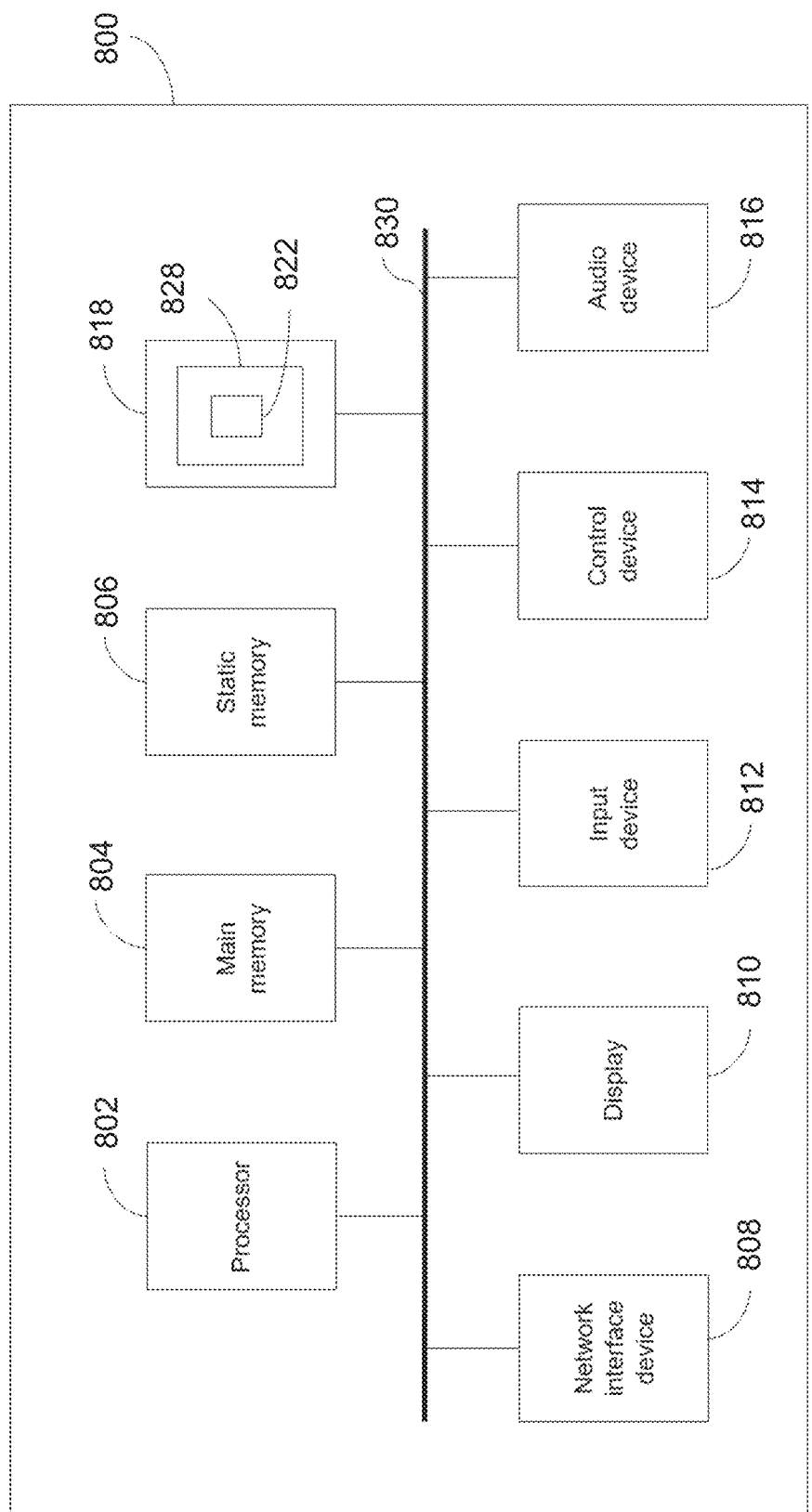
FIG. 12 depicts an example implementation of a computing device according to the present disclosure.

FIG. 12 illustrates a block diagram of one implementation of a computing device 800 within which a set of instructions, for causing the computing device to perform any one or more of the methodologies discussed herein, may be executed. In alternative implementations, the computing device may be connected (e.g., networked) to other machines in a Local Area Network (LAN), an intranet, an extranet, or the Internet. The computing device may operate in the capacity of a server or a client machine in a client-server network environment, or as a peer machine in a peer-to-peer (or distributed) network environment. The computing device may be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single computing device is illustrated, the term "computing device" shall also be taken to include any collection of machines (e.g., computers) that individually or jointly execute a set (or multiple sets) of instructions to perform any one or more of the methodologies discussed herein. The computing device 800 may correspond to the controller or control device as described herein.

The example computing device 800 includes a processing device 802, a main memory 804 (e.g., read-only memory (ROM), flash memory, dynamic random access memory (DRAM) such as synchronous DRAM (SDRAM) or Rambus DRAM (RDRAM), etc.), a static memory 806 (e.g., flash memory, static random access memory (SRAM), etc.), and a secondary memory (e.g., a data storage device 818), which communicate with each other via a bus 830.

Processing device 802 represents one or more general-purpose processors such as a microprocessor, central processing unit, or the like. More particularly, the processing device 802 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 802 may also be one or more special-purpose processing devices such as an application specific integrated circuit (ASIC), a field programmable gate array (FPGA), a digital signal processor (DSP), network processor, or the like. Processing device 802 is configured to execute the processing logic (instructions 822) for performing the operations and steps discussed herein.

The computing device 800 may further include a network interface device 808. The computing device 800 also may include a video display unit 810 (e.g., a liquid crystal display (LCD) or a cathode ray tube (CRT)), an alphanumeric input device 812 (e.g., a keyboard or touchscreen), a cursor control device 814 (e.g., a mouse or touchscreen), and an audio device 816 (e.g., a speaker).

The data storage device 818 may include one or more machine-readable storage media (or more specifically one or more non-transitory computer-readable storage media) 828 on which is stored one or more sets of instructions 822 embodying any one or more of the methodologies or functions described herein. The instructions 822 may also reside, completely or at least partially, within the main memory 804 and/or within the processing device 802 during execution thereof by the computer system 800, the main memory 804 and the processing device 802 also constituting computer-readable storage media.

The various methods described above may be implemented by a computer program. The computer program may include computer code arranged to instruct a computer to perform the functions of one or more of the various methods described above. The computer program and/or the code for performing such methods may be provided to an apparatus, such as a computer, on one or more computer readable media or, more generally, a computer program product. The computer readable media may be transitory or non-transitory. The one or more computer readable media could be, for example, an electronic, magnetic, optical, electromagnetic, infrared, or semiconductor system, or a propagation medium for data transmission, for example for downloading the code over the Internet. Alternatively, the one or more computer readable media could take the form of one or more physical computer readable media such as semiconductor or solid state memory, magnetic tape, a removable computer diskette, a random access memory (RAM), a read-only memory (ROM), a rigid magnetic disc, and an optical disk, such as a CD-ROM, CD-R/W or DVD.

In an implementation, the modules, components and other features described herein can be implemented as discrete components or integrated in the functionality of hardware components such as ASICS, FPGAs, DSPs or similar devices.

A "hardware component" is a tangible (e.g., non-transitory) physical component (e.g., a set of one or more processors) capable of performing certain operations and may be configured or arranged in a certain physical manner. A hardware component may include dedicated circuitry or logic that is permanently configured to perform certain operations. A hardware component may be or include a special-purpose processor, such as a field programmable gate array (FPGA) or an ASIC. A hardware component may also include programmable logic or circuitry that is temporarily configured by software to perform certain operations.

Accordingly, the phrase "hardware component" should be understood to encompass a tangible entity that may be physically constructed, permanently configured (e.g., hardwired), or temporarily configured (e.g., programmed) to operate in a certain manner or to perform certain operations described herein.

In addition, the modules and components can be implemented as firmware or functional circuitry within hardware devices. Further, the modules and components can be implemented in any combination of hardware devices and software components, or only in software (e.g., code stored or otherwise embodied in a machine-readable medium or in a transmission medium).

Unless specifically stated otherwise, as apparent from the following discussion, it is appreciated that throughout the description, discussions utilizing terms such as "receiving", "determining", "comparing", "enabling", "maintaining," "identifying," "applying," "transmitting," "generating," or the like, refer to the actions and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The approaches described herein may be embodied on a computer-readable medium, which may be a non-transitory computer-readable medium. The computer-readable medium may carry computer-readable instructions arranged for execution upon a processor so as to cause the processor to carry out any or all of the methods described herein.

The term "computer-readable medium" as used herein refers to any medium that stores data and/or instructions for causing a processor to operate in a specific manner. Such storage medium may comprise non-volatile media and/or volatile media. Non-volatile media may include, for example, optical or magnetic disks. Volatile media may include dynamic memory. Exemplary forms of storage medium include, a floppy disk, a flexible disk, a hard disk, a solid state drive, a magnetic tape, or any other magnetic data storage medium, a CD-ROM, any other optical data storage medium, any physical medium with one or more patterns of holes, a RAM, a PROM, an EPROM, a FLASH-EPROM, NVRAM, and any other memory chip or cartridge.

It is to be understood that the above description is intended to be illustrative, and not restrictive. Many other implementations will be apparent to those of skill in the art upon reading and understanding the above description. Although the present disclosure has been described with reference to specific example implementations, it will be recognized that the disclosure is not limited to the implementations described, but can be practiced with modification and alteration within the scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

The invention claimed is:

1. A computer-implemented method for cancer treatment comprising:
    calculating, over a sliding window comprising a plurality of timepoints of a radiotherapy treatment, a positional error between:
        a measured target position signal determined from a series of images and sampled at acquisition times of the images, wherein the measured target position signal is time-shifted to compensate for system latency; and
        an estimated target position signal; and
    generating a computer-executable instruction configured to alter the radiotherapy treatment in response to the positional error violating a threshold, wherein:
        the positional error includes a mean error, the mean error being calculated as the absolute difference between the mean of the measured target position signal sampled at the acquisition times of the images and the mean of the estimated target position signal, for the sliding window of the radiotherapy treatment; or
        the positional error includes a standard deviation error, the standard deviation error being calculated as the absolute difference between the standard deviation of the measured target position signal sampled at the acquisition times of the images and the standard deviation of the estimated target position signal, for the sliding window of the radiotherapy treatment.

2. The computer-implemented method of claim 1, wherein the positional error is calculated as the sum of the mean error and the standard deviation error.

3. The computer-implemented method of claim 1, wherein the computer-executable instruction is configured to interrupt the radiotherapy treatment, or wherein the computer-executable instruction is configured to vary a dose rate of the radiotherapy treatment in dependence on the positional error.

4. The computer-implemented method of claim 1, wherein:
    the estimated target position signal corresponds to a predicted anatomical position of a target based on a prediction model, the prediction model being based on measured positions of the target at previous timepoints; or
    wherein the estimated target position signal corresponds to an anatomical position of a target based on measured positions of the target at previous timepoints not compensated for system latency.

5. The computer-implemented method of claim 1, wherein the threshold is determined based on a correlation between positional errors and dosimetric errors for one or more test sets of data.

6. The computer-implemented method of claim 1 comprising, in response to the threshold being violated:
    starting a counter; and
    if the positional error violates the threshold within a pre-determined time period, resetting the counter to zero at a timepoint at which the threshold is violated;
    if the positional error does not violate the threshold within the pre-determined time period, resuming radiotherapy treatment in accordance with a pre-determined treatment plan.

7. The computer-implemented method of claim 1, comprising calculating a respective positional error for each of multiple spatial dimensions.

8. The computer-implemented method of claim 7, comprising generating the computer-executable instruction configured to alter the radiotherapy treatment in response to at least one of the positional errors violating a respective threshold, or in response to a sum of the positional errors violating a combined threshold.

9. A non-transitory computer-readable medium encoded with a computer program for cancer treatment which, when executed by a processor, causes the processor to:
    calculate, over a sliding window comprising a plurality of timepoints of a radiotherapy treatment, a positional error between:
        a measured target position signal determined from a series of images and sampled at acquisition times of the images, wherein the measured target position signal is time-shifted to compensate for system latency; and
        an estimated target position signal; and
    generate a computer-executable instruction configured to alter the radiotherapy treatment in response to the positional error violating a threshold, wherein:
        the positional error includes a mean error, the mean error being calculated as the absolute difference between the mean of the measured target position signal sampled at the acquisition times of the images and the mean of the estimated target position signal, for the sliding window of the radiotherapy treatment; or
        the positional error includes a standard deviation error, the standard deviation error being calculated as the absolute difference between the standard deviation of the measured target position signal sampled at the acquisition times of the images and the standard deviation of the estimated target position signal, for the sliding window of the radiotherapy treatment.

10. A control device configured to be communicatively coupled to a radiation source of a radiotherapy device and a position sensor of the radiotherapy device, the control device comprising a processor and computer-executable instructions for cancer treatment which, when executed by the processor, cause the control device to:
    calculate, over a sliding window comprising a plurality of timepoints of a radiotherapy treatment, a positional error between:
        a measured target position signal determined from a series of images and sampled at acquisition times of the images, wherein the measured target position signal is time-shifted to compensate for system latency; and
        an estimated target position signal; and
    generate a computer-executable instruction configured to alter the radiotherapy treatment in response to the positional error violating a threshold, wherein:

the positional error includes a mean error, the mean error being calculated as the absolute difference between the mean of the measured target position signal sampled at the acquisition times of the images and the mean of the estimated target position signal, for the sliding window of the radiotherapy treatment; or the positional error includes a standard deviation error, the standard deviation error being calculated as the absolute difference between the standard deviation of the measured target position signal sampled at the acquisition times of the images and the standard deviation of the estimated target position signal, for the sliding window of the radiotherapy treatment.

11. The control device of claim 10, wherein the control device is part of the radiotherapy device comprising:
the radiation source configured to generate a radiotherapy beam for the radiotherapy treatment; and
the position sensor configured to determine the measured target position signal.

12. The control device of claim 10, wherein the computer-executable instruction is configured to interrupt the radiotherapy treatment, or wherein the computer-executable instruction is configured to vary a dose rate of the radiotherapy treatment in dependence on the positional error.

13. The control device of claim 10, wherein:
the estimated target position signal corresponds to a predicted anatomical position of a target based on a prediction model, the prediction model being based on measured positions of the target at previous timepoints; or
wherein the estimated target position signal corresponds to an anatomical position of a target based on measured positions of the target at previous timepoints not compensated for system latency.

14. The control device of claim 10, wherein the threshold is determined based on a correlation between positional errors and dosimetric errors for one or more test sets of data.

15. The control device of claim 10, configured, in response to the threshold being violated, to:
start a counter; and
if the positional error violates the threshold within a pre-determined time period, reset the counter to zero at a timepoint at which the threshold is violated;
if the positional error does not violate the threshold within the pre-determined time period, resume radiotherapy treatment in accordance with a pre-determined treatment plan.

16. The control device of claim 10, configured to calculate a respective positional error for each of multiple spatial dimensions.

17. The control device of claim 16, wherein the computer-executable instruction is configured to alter the radiotherapy treatment in response to at least one of the positional errors violating a respective threshold, or in response to a sum of the positional errors violating a combined threshold.

* * * * *